United States Patent
Hattery et al.

(10) Patent No.: US 7,920,908 B2
(45) Date of Patent: Apr. 5, 2011

(54) MULTISPECTRAL IMAGING FOR QUANTITATIVE CONTRAST OF FUNCTIONAL AND STRUCTURAL FEATURES OF LAYERS INSIDE OPTICALLY DENSE MEDIA SUCH AS TISSUE

(76) Inventors: David Hattery, Washington, DC (US);
Brenda Hattery, Washington, DC (US)

( * ) Notice: Subject to any disclaimer, the term of this patent is extended or adjusted under 35 U.S.C. 154(b) by 1754 days.

(21) Appl. No.: 10/965,209

(22) Filed: Oct. 15, 2004

(65) Prior Publication Data
US 2005/0273011 A1 Dec. 8, 2005

Related U.S. Application Data

(60) Provisional application No. 60/511,325, filed on Oct. 16, 2003, provisional application No. 60/542,301, filed on Feb. 9, 2004.

(51) Int. Cl.
*A61B 5/05* (2006.01)
(52) U.S. Cl. ........................................ 600/407; 600/443
(58) Field of Classification Search ........... 600/407–480
See application file for complete search history.

(56) References Cited

U.S. PATENT DOCUMENTS

| | | | | |
|---|---|---|---|---|
| 5,865,754 | A * | 2/1999 | Sevick-Muraca et al. | 600/476 |
| 6,335,792 | B1 * | 1/2002 | Tsuchiya | 356/432 |
| 6,419,361 | B2 * | 7/2002 | Cabib et al. | 351/221 |
| 7,158,097 | B2 * | 1/2007 | Taylor et al. | 345/8 |
| 7,186,984 | B2 * | 3/2007 | Bonnin et al. | 250/369 |
| 7,239,903 | B2 * | 7/2007 | Eda | 600/310 |
| 2003/0053674 | A1 * | 3/2003 | Armato et al. | 382/132 |
| 2003/0208169 | A1 * | 11/2003 | Chaiken et al. | 604/310 |
| 2004/0052409 | A1 * | 3/2004 | Bansal et al. | 382/128 |
| 2005/0041842 | A1 * | 2/2005 | Frakes et al. | 382/128 |
| 2005/0251039 | A1 * | 11/2005 | Chalana et al. | 600/437 |

OTHER PUBLICATIONS

S. G. Demos and R. R. Alfano. Temporal gating in highly scattering media by the degree of optical polarization. *Optics Letters*, 21(2):161-163, Jan. 1996.
S. G. Demos and R. R. Alfano. Optical Polarization Imaging. *Applied Optics*, 36:150-155, 1997.

(Continued)

*Primary Examiner* — Brian Casler
*Assistant Examiner* — Nasir Shahrestani
(74) *Attorney, Agent, or Firm* — MDIP LLC

(57) ABSTRACT

A method for the evaluation of target media parameters in the visible and near infrared is disclosed. The apparatus comprises a light source, an illuminator/collector, optional illumination wavelength selector, an optional light gating processor, an imager, detected wavelength selector, controller, analyzer and a display unit. The apparatus illuminates an in situ sample of the target media in the visible through near infrared spectral region using multiple wavelengths and gated light. The sample absorbs some of the light while a large portion of the light is diffusely scattered within the sample. Scattering disperses the light in all directions. A fraction of the deeply penetrating scattered light exits the sample and may be detected in an imaging fashion using wavelength selection and an optical imaging system. The method extends the dynamic range of the optical imager by extracting additional information from the detected light that is used to provide reconstructed contrast of smaller concentrations of chromophores. The light detected from tissue contains unique spectral information related to various components of the tissue. Using a reiterative calibration method, the acquired spectra and images are analyzed and displayed in near real time in such a manner as to characterize functional and structural information of the target tissue.

26 Claims, 21 Drawing Sheets

OTHER PUBLICATIONS

S. G. Demos, A. J. Papadopoulos, H. Savage, A. S. Heerdt, S. Schantz and R. R. Alfano. Polarization filter for biomedical tissue optical imaging. *Photochemistry and Photobiology*, 66(6):821-5, Dec. 1997.

Stavros G. Demos, Harry B. Radousky and Robert R. Alfano. Deep subsurface imaging in tissues using spectral and polarization filtering. *Optics Express*, 7(1):23-28, Jul. 2000.

A. H. Gandjbakche and G. H. Weiss. Random walk and diffusion-like models of photon migration in turbid media. In E. Wolf, editor, *Progress in Optics*, vol. 34, chapter 4, pp. 333-402. Elsevier, Amsterdam, 1995.

S. L. Jacques. Skin Optics. *Oregon Medical Laser Center News*, 1998. http://omlc.ogi.edu/news/jan98/index.htrnl.

S. L. Jacques and D. J. McAuliffe. The melanosome: threshold temperature for explosive vaporization and internal absorption coefficient during pulsed laser irradiation. *Photochemistry and Photobiology*, 53:769-775, 1991.

S. L. Jacques, J. R. Roman and K. Lee. Imaging superficial tissues with polarized light. *Lasers in Surgery and Medicine*, 26(2):119-29, 2000.

S. P. Morgan, M. P. Khong and M. G. Somekh. Effects of polarization state and scatterer concentration on optical imaging through scattering media. *Applied Optics*, 36:1560-1565, 1997.

Stephen P. Morgan and M. E. Ridgway. Polarization properties of light backscattered from a two layer scattering medium. *Optics Express*, 7(12):395-402, Dec. 2000.

I. S. Saidi, S. L. Jacques and F. K. Tittle. Mie and Rayleigh Modeling of Visible-light Scattering in Neonatal Skin. *Applied Optics*, 34(31):7410-7418, 1995.

J. M. Schmitt, A. H. Gandjbakhche and R. F. Bonner. Use of polarized light to discriminate short-path photons in a multiply scattering medium. *Applied Optics*, 31(30):6535-6546, 1992.

S. Wray, M. Cope, D. T. Delpy, J. S. Wyatt and E. O. R. Reynolds. Characterization of the near infrared absorption spectra of cytochrome aa3 and haemoglobin for the non-invasive monitoring of cerebral oxygenation. *Biochimica et Biophsica Acta*, 933:184-192, 1988.

K. M. Yoo and R. R. Alfano. Photon localization in a disordered multilayered system. *Physical Review B Condensed Matter*, 39(9):5806-5809, Mar. 1989.

Gang Yao and Lihong V. Wang. Propagation of polarized light in turbid media: simulated animation sequences. *Optics Express*, 7(5):198-203, Aug. 2000.

* cited by examiner

MULTISPECTRAL IMAGING FOR QUANTITATIVE CONTRAST OF FUNCTIONAL AND STRUCTURAL FEATURES OF LAYERS INSIDE OPTICALLY DENSE MEDIA SUCH AS TISSUE

BACKGROUND OF THE INVENTION

1. Field of the Invention

The field of the invention relates to quantitative optical spectroscopic imaging, and more particularly, to a method of obtaining functional and structural information from multispectral images of in situ analyzed multi-layered, optically dense samples.

2. Background Information

Reflectance Spectroscopy

In general, reflectance spectroscopy is concerned with the identification of a chemical structure comprising a sample through the use of reflected information. Diffuse reflectance spectroscopy is also generally known, and is widely used in the visible to infrared regions of the light spectrum to study materials to include, but not limited to, grains and other food products.

In broad terms, diffuse reflectance spectroscopy utilizes the fact that the sample materials will tend to scatter light in a more or less random fashion. A fraction of the light will eventually be scattered back from the sample and collected by a detector to provide a quantitative or qualitative representation of the sample.

In infrared spectroscopy it is often desirable to use the mid-infrared region of the spectrum. The fundamental vibrational absorptions are strongest here, in the infrared region. The goal of infrared spectroscopy sampling is often to prepare a sample so that it may be analyzed within this mid-infrared light. Reflectance spectroscopy is one very popular way of making a sample compatible with mid-infrared light. If a sample is too thick to get any light through in transmission, often a result can be obtained by reflectance. Reflectance spectroscopy is complicated, however, by the fact that there is more than one optical phenomenon occurring in this mode.

Reflectance of light from a sample can be largely divided into two categories, diffuse reflectance and specular reflectance. The specular reflectance of a sample is the light which does not propagate into the sample, but rather reflects "like a mirror" from the front surface of the sample. This component contains information about the sample at the surface. While the specular component does not physically appear much like an absorbance spectrum, it can be related to the absorbance spectrum of the bulk material through a transformation called the Kramers-Kronig transformation. Still most experts agree that the diffuse component is much more useful for sample qualification and quantification than the specular component. There has been much effort to enhance the diffuse component, to deemphasize the specular component and to essentially cause the reflectance spectrum to be more transmission-like.

Generally these efforts fall largely into three categories: optical discrimination against specular, mechanical discrimination, and secondary methods of sample preparation designed to minimize specular. A fourth non-independent approach is to move away from the mid-infrared region in order to relax the sample preparation requirements. By moving to the near-infrared or visible region of the spectrum, the vibrational spectroscopy becomes more blunt and imprecise, but often this can be made up for by the improvements observed in the quality and signal-to-noise ratio of the data obtained because of improved sampling ability, more appropriate path length, and better discrimination against specular reflectance. This approach is especially useful when quantitative information is desired.

Most experts would agree that the diffuse component is desirable, and even essential, if the sample is thick, layered or non-homogenous.

Light spectroscopic methods are critical to advances in molecular characterization of disease processes. However, most of these methods have been limited to in-vitro or cell culture studies. In fact, strong scattering in almost all tissue types causes dispersion of the photons paths. Hence, quantitative analysis of spectral data obtained from structures below the tissue surface requires accounting for scattering which is a function of wavelength and affects both the penetration of the photons and the pathlengths over which the photons will be subject to molecularly specific absorption.

The goal of much current research is to non-invasively obtain diagnostically useful molecular information from embedded sites. The use of spectroscopic techniques to aid in the diagnosis of various diseases has been limited due to complications arising from the scattering of light in tissue. Traditional spectroscopy relies upon geometrical optics to keep the relative paths of the photons consistent and thus the absorptive effect of analytes may be obtained directly using Beer's law. The scattering of light causes dispersion in the length of the path taken by photons traveling through the tissue. Thus, some photons will travel shorter direct paths and some will travel longer paths. Further, the degree of scatter-induced dispersion is often a function of wavelength.

To reduce the scatter-induced dispersion, many researchers employ devices to limit detected photons to those with more uniform path lengths. This is traditionally accomplished using special optics such as confocal lenses and pinholes. Such methods. are generally limited to depths less than 0.1 mm which is approximately the thickness of the epidermis. More recently, researchers are fixing the source and detector separation by using fiber probes, or special optics and either point illumination with one or more detectors at a fixed distance, or point detection with one or more sources at a fixed distance. By using random or probabilistic methods, information from sites below the epidermis may be obtained. These probes, however, often require direct contact with the patient's skin. Generating an image with such a system typically requires a scanning system which successively probes points on the tissue surface and combines them into an image. This results in long image generation times and the potential for patient motion to create artifacts.

Other researchers employ infrared sensitive multispectral imagers. In the infrared, penetration into the tissue is typically less than 100 microns. The shallow penetration greatly limits potential applications since many anomalous sites are deeper. Due to low absorption, visible and near infrared wavelengths (NIR) light penetrates much deeper with NIR capable of passing through 10 cm or more. What is needed is a non-contact method that uses broad area illumination with multispectral imaging that can provide quantified data on analyte concentrations at points below the epidermis in vivo.

For light to reach an anomalous region in the body it must usually pass through the epidermis. Jacques has shown that the absorption of light in the epidermis is a function of the melanin content in the epidermis. The absorption spectrum for melanin $\mu_{a(mel)}(\lambda)$ is shown in FIG. 1 (in units of mm$^{-1}$ which will be used throughout for absorption and scattering coefficients) [2].

Saidi [3] has published absorption data for de-melaninized skin. All other skin analytes are combined into this single absorption variable $\mu_{a(skin)}(\lambda)$ which is a function of wavelength as shown in FIG. 2. The dominant chromophores in this absorption spectrum are lipids and water.

Now that the absorption spectra of the main analytes in the epidermis have been defined, Jacques defines the total absorption of the epidermis as:

$$\mu_{a(epi)}(\lambda) = V_{mel}\mu_{a(mel)}(\lambda) + (1-V_{mel})\mu_{a(skin)}(\lambda) \quad (1)$$

where $V_{mel}$ is the volume fraction of melanin which offsets the amount of de-melaninized skin and $\mu_{a(mel)}(\lambda)$ is the absorption spectra of melanin.

Jacques and others have shown that the absorption of blood is a function of the volume fraction of oxy-and deoxy-hemoglobin, $V_{oxy}$ and $1-V_{oxy}$ respectively. This blood volume is confined to the sub-epidermal dermis. The relative absorption spectra for each type of hemoglobin $\mu_{a(oxy)}(\lambda)$ and $\mu_{a(deoxy)}(\lambda)$ as published by Wray [4] are shown in FIG. 3. The total blood absorption $\mu_{a(blood)}(\lambda)$ may be expressed as a volume-based combination of the two:

$$\mu_{a(blood)}(\lambda) = V_{oxy}\mu_{a(oxy)}(\lambda) + (1-V_{oxy})\mu_{a(deoxy)}(\lambda) \quad (2)$$

The total absorption of the dermis from Jacques is therefore:

$$\mu_{a(derm)}(\lambda) = V_{blood}\mu_{a(blood)}(\lambda) + (1-V_{blood})\mu_{a(skin)}(\lambda) \quad (3)$$

Random Walk theory has been used to model the motion of light in high scattering, low absorption media such as tissue. The diffuse reflectance from a collimated point source of illumination has been shown by Gandjbakhche [1]:

$$R = \frac{e^{-\sqrt{24\mu_{a(layer)}/\mu'_{a(layer)}}}}{\sqrt{24\mu_{a(layer)}/\mu'_{s(layer)}}} \left[ 1 - e^{-\sqrt{24\mu_{a(layer)}/\mu'_{a(layer)}}} - 2\frac{1-\cosh[\sqrt{24\mu_{a(layer)}/\mu'_{a(layer)}}]}{1-e^{L\sqrt{24\mu_{a(layer)}/\mu'_{a(layer)}}}} \right] \quad (4)$$

where $\mu'_s(\lambda)$ is the transport-corrected scattering coefficient which is a function of wavelength and L is a non-dimensional measure of the thickness of the tissue layer. Jacques has expressed the wavelength dependence is a linear combination of the Raleigh, $2\times10^4\lambda^{-2.5}$ [mm$^{-1}$], and Mie, $2\times10^{21}\lambda^{-4}$ [mm$^{-1}$], scattering components:

$$\mu'_s(\lambda) \approx 2\times10^4\lambda^{-2.5} + 2\times10^{21}\lambda^{-4} \quad (5)$$

It is the wavelength dependence of $\mu'_s(\lambda)$, which is shown in FIG. 4, that makes tissue spectroscopy difficult. The effect of changes in $\mu'_s(\lambda)$ are tightly linked to changes in the $\mu_a(\lambda)$ components as may be seen in Eq. 4.

Use of such equations can make possible the ability to obtain diagnostically useful molecular information from embedded sites in a non-invasive manner.

In contrast to the present invention, other studies using various imaging technologies are not capable of accessing tissue utilization of specific informative analytes, are limited to only indirect assessment of tissue status, are labor intensive and/or time-consuming, are susceptible to extrinsic variances such as room or patient temperature, are limited in their utility to only highly vascularized tissue, and are cost prohibitive and/or lack portability (See, e.g., U.S. application Ser. No. 2003/0139667).

Calibration of an imaging system is a crucial but under-emphasized aspect of system performance. The calibration data is a set of weights that normalize system sensitivity to some arbitrary normal. The system sensitivity is a combination of the amount of energy in a particular filter band that is emitted by the light source with the integrated sensitivity of the detector to that energy. Each of those components is generally not known, the net response is traditionally estimated by imaging a calibrated or known reflectance standard.

This type of calibration must be repeated often since the spectral characteristics of the source lamp may change with environment and lamp age. Yet, because of its time-consumption and inconvenience, calibration may not be performed as frequently as needed to assure good results.

Changes in light source spectral characteristics (intensity as a function of wavelength) during a given session can even reduce the effectiveness of calibration methods performed during each imaging session.

What is needed is a method for calibration that can be used without needing pre-or post-data collection hardware calibration information.

Extending Dynamic Range of Imaging Sensors

Traditionally, scientific applications of multispectral image processing has employed monochrome charge coupled devices (CCD). Complementary Metal-Oxide Semiconductor or CMOS detectors, offers an inexpensive alternative to CCDs. The cost of CMOS sensors is rapidly dropping due to high production volumes. In addition to still and video cameras, CMOS imagining sensors are being embedded in computers, personal digital assistants (PDAs) and even cell phones (40 million cameras in cell phones and 30 million still cameras sold 2003). CCD sensors have been used for scientific work due to their characteristic high dynamic range (12 to 16 bits) and low noise for long exposure. Production volumes of CCD chips are relatively stagnant due to the requirement for custom fabrication facilities which keeps CCD chip costs high. CMOS sensors have the benefit of being manufactured on the dynamically improving and expanding CMOS fabrication facility base. While the performance of CMOS sensors has been improving dramatically, CMOS sensors typically have less dynamic range than CCD devices due to the less demanding requirements of consumer products (typically 8 to 12 bits of dynamic range). However, CMOS devices have the large benefit of being able to create sophisticated smart sensors.

Compared to scientific grade CCD cameras, most CMOS sensors are designed for color imaging. The traditional approach for implementing color in both CCD and CMOS devices is to place a pattered filter, or Bayer filter, over the chip which passes specific wavelengths of light to each pixel. Thus, for example, a pixel that primarily detects red light will typically have two neighboring pixels that primarily detect green, and another neighboring pixel that detects blue. The specific four pixel pattern of two green, one red and one blue is generally repeated across the face of the image sensor. The camera contains a processor that interpolates the blue and green values it should use at a red pixel location from the respective color of neighboring pixels. This process of interpolation is repeated at each pixel to obtain the colors missing at each pixel. Such interpolation filtering is typically designed to produce visually appealing color rendering in images and may require 100 calculations at each pixel (depending on the algorithm and the desire to avoid visually distracting artifacts in the resulting images).

Some recent CMOS image sensor designs by Foveon bypass the Bayer filter approach and instead use a layered CMOS sensor in which the depth of photon penetration before detection is used to assign color. Blue is generally detected near the surface and red photons penetrate deepest before detection. These devices obviate the need for color interpolation, but are reported to have colors that are less well separated than possible with Bayer filters.

A pixel on a digital camera sensor collects photons which are converted into an electrical charge by its photodiode. Once the "bucket" is full, the charge caused by additional photons will overflow and have no effect on the pixel value, resulting in a clipped, overexposed, or saturated pixel value. Blooming occurs when this charge flows over to surrounding pixels, brightening or overexposing them in the process. Bloom can be a problem even in CCD devices that have anti-bloom circuitry. CMOS detectors have a big advantage over CCD sensors in that bloom is virtually nonexistent. Thus, saturation of a pixel has minimal effect on the neighboring pixels.

To extend dynamic range of an image or image-based system, the use of multiple varying exposures, or exposure bracketing, is known (see, for example, U.S. Pat. application Ser. No. 20030078737). In contrast to the present invention, others using these exposure-based techniques employ them in a simple manner qualitatively to enhance rendering contrast or in a manner of thresholding to quantify detected signal strength, and without employing knowledge of the imager filters' spectral response functions for added and quantifiable dynamic range.

Accordingly, what is needed is a non-invasive means of determining the functional and structural status of in situ optically dense samples such as tissues in a non-subjective manner using reflectance or transmission image-based spectroscopy. Further, such a means should also provide long term non-subjective assessment of the in situ sample in response to various conditions such as age, environment, trauma, as well as treatment modalities, including the therapeutic effectiveness of pharmaceuticals.

Moreover, methods and devices which exploit various types of attenuation factors and commensurate dynamic range gains for illumination bands in the visual to infrared light spectrum also need to be developed.

The present invention satisfies these needs, as well as others.

SUMMARY OF THE INVENTION

The present invention is directed to improved measurement and analysis of multi-layered, optically dense samples using transillumination and/or diffusely reflected light with differential pathlength corrected spectroscopy, while eliminating the effects of surface reflected light and other light not reflected from deep within an optically dense medium. Further, a device is described, along with commensurate methods, which extends the dynamic range of imaging detector/sensors.

The present invention discloses a method of imaging an object such as an anomalous condition in the body; including the steps of:

(a) acquiring a plurality of image datasets of the area of interest;

(b) calibrating the imaging system;

(c) for each of the image datasets, transforming spectral image data into relative concentrations of analytes in tissue and/or structural parameters by: (i) building a model inclusive of parameters of interest and with corrections for layers and scattering, and (ii) convolving analyte spectra with the spectral response functions of the imager being used; (iii) fitting acquired datasets to the model; in this step, the model may be run iteratively with interim steps in which spatial filtering may be used to enforce physiologically relevant patterns;

(d) converting and/or linearly or nonlinearly combining transformed data to form output images.

The invention is a non-contact, in vivo method for quantifying chromophore concentrations, functional, and/or structural parameters of optically dense samples, such as tissue, from multispectral images that accounts for the change in path length as a function of wavelength, and hence the change in exposure to absorption by specific chromophores. The method allows one to quantify concentration of chromophores at various depths. The accuracy of the quantification is much better than possible with methods which don't account for changes in path length dispersion as a function of wavelength (i.e., implies pathlength correction). The quantification accuracy is dependent on calibration, but we have devised a forward-model calibration which can provide relative changes in chromophore concentration-quantitative contrast—that can be used to track such things as changes in tissue function at anomalous sites. This method is designed to work for highly scattering media, such as tissue. Where absorption is relatively low, such as the NIR in tissue, useful signals will be obtained from objects at the sample surface to those at depths of 1 cm or more. This permits biochemically specific analysis of many diseases and anomalous conditions in humans and animals since much of the body's volume and its respective diseases are located within 1 cm of the tissue surface.

The method transforms spectral image data into relative concentrations of chromophores in tissue and/or analytes, functional or structural parameters; these relative concentrations and parameters can provide both structural and functional contrast useful to the diagnosis and monitoring of disease or anomalies. Point measurements suffer in accuracy because the absolute value of the various analyte concentrations in "normal" tissue and "tumors" vary over a wide range in humans and has been shown to be a function of a number of cycles such as time of day, month or menstrual cycle, and age, as well as metabolism; analyte concentrations at any point in such cycles is still highly variable between individuals. Nonetheless, tumors generally manifest distinctly different metabolism-related parameters from normal tissue in each individual even if the absolute values of normal and tumor parameters overlap in the general population. Thus, point measurements are more difficult to use than images which show the spatial changes in parameters and are therefore compensating for each individuals unique normals. The method employs a layered model of the skin in which specific analytes exist in specific layers. The spectral signatures of analytes such as oxy-and deoxy-hemoglobin, oxy and redox cytochromes b, and c, and melanin are known. To obtain information on the concentration of those and other analytes in the tissue, however, the diffuse reflectance NIR images from the patients must be corrected for scattering. The scattering is modeled using analytical solutions developed from a random walk model of photon migration in turbid media. When the multispectral patient data is fit to the model, physiologically related parameters, such as to blood volume and oxygenation, are obtained. This provides clinically important data that may be used by the physician for evaluations of drug effectiveness, disease assessment and patient treatment monitoring.

There has thus been outlined, rather broadly, the more important features of the invention in order that the detailed description may be better understood, and in order that the present contribution to the art may be better appreciated.

There are additional features of the invention that will be described below. In this respect, before explaining at least one embodiment of the invention in detail, it is to be understood that the invention is not limited in its application to the details of that example. The invention is capable of other embodiments and of being practiced and carried out in various ways. Also, it is to be understood that the phraseology and terminology employed herein are for the purpose of the description and should not be regarded as limiting.

A primary object of the present invention is to overcome inaccuracies in the current tissue spectroscopy methods due to wavelength-based changes in scattering.

Another object of the present invention is to employ area multispectral images (rather than point measurements) to diagnose, monitor, or survey large areas of interest quickly.

Another object of the present invention is to overcome inaccuracies in the current tissue spectroscopy methods due to the presence of layers in which specific analytes are confined (rather than distributed uniformly).

Another object of the present invention is to build a method in which analytes or parameters may be added and/or removed easily to/from the model.

Another object of the present invention is to present a method for forward model calibration that can be used anytime an analytical model exists for a set of data or measurements without needing pre-or post-data collection hardware calibration information.

Another object of the present invention is to present a method for forward model calibration of images from multispectral hardware without needing pre-or post-image hardware calibration information.

Other objects and advantages of the present invention will become obvious to the reader and it is intended that these objects and advantages are within the scope of the present invention.

It is another object of the present invention to exploit the bloom resistance of CMOS sensors, as well as extending the effective dynamic range of such sensors.

In another aspect, the present invention envisages methods which can utilize both Bayer filters and Foveon chips.

In one embodiment a method of imaging an optically dense medium is envisaged, including illuminating the medium with multiple wavelengths of filtered, processed light, comparing collected wavelengths, reconstructing local concentration variations of absorbing/light-scattering components comprising the medium, calibrating the image by iteratively integrating parameters for each reconstruction point. In a related aspect, calibrating includes, arbitrarily assigning, at each pixel within an image, parameter values to each known component comprising the medium, where parameter values are selected from a plurality of values, executing an algorithm to converge a calibration function, including calculating calibration coefficients by fixing one or more parameters at one value and solving for other one or more parameters, thereby obtaining average calibration loop pixel parameter values, estimating the convergence between the fixed one or more parameter values and the other one or more parameter values, adjusting the calibration by imposing one or more spatial characteristics for the fixed one or more parameter values to smooth said values and repeating the steps above until one or more predetermined conditions are satisfied. In a further related aspect, reconstructed data recovered is converted to form output images.

In another aspect, converting is carried out according to the relationship:

$$I_{detected}(\lambda) = c I_{source}(\lambda) d(\lambda) \frac{1 - e^{-\sqrt{A\mu_{a(bottom)}(\lambda)/\mu'_{a(bottom)}(\lambda)}}}{\sqrt{A\mu_{a(bottom)}(\lambda)/\mu'_{a(bottom)}(\lambda)}} e^{-2t_{top}\mu_{a(top)}(\lambda)} \quad (6)$$

where:

$I_{detected}(\lambda)$ denotes the intensity of the medium under examination at a defined wavelength;

c denotes an intensity scaling variable;

$I_{source}(\lambda)$ denotes the intensity of the collimated light source;

$d(\lambda)$ denotes the spectral response of the camera;

$\mu'_{s(bottom)}(\lambda)$ denotes transport corrected scattering coefficient of the bottom layer;

A denotes a light and tissue interaction geometry factor;

$\mu_{a(bottom)}(\lambda)$ denotes the absorption coefficient for the bottom layer;

$t_{top}$ denotes thickness of a thin overlaying region; and $\mu_{a(top)}(\lambda)$ denotes the absorption coefficient for the top layer.

In another related aspect, the collected wavelengths are selectively processed to remove reflected light that corresponds to very short photon pathlengths, for example, but not limited to light selectively processed by one or more gated optical imagers or one or more polarizers. Further, comparing is envisaged to comprise comparing the collected wavelengths to one or more mixtures of known spectra.

In a related aspect, the illuminating light of is polarized. In another aspect, the light is modulated to reduce extraneous background light.

In one aspect, parameter values are envisaged to include intensity of light reaching the medium surface, chromophore volume fraction comprising one or more layers of the medium, thickness of one or more layers of the medium, or changes in concentration of the one or more chromophores, or a combination of one or more thereof.

In another aspect, the multiple wavelengths comprise wavelengths in the visible and near-infrared (NIR) spectra. For example, these wavelengths may include, but are not limited to, between about 400 nm and about 2700 nm. In a related aspect, the medium is illuminated with at least two different wavelengths or as many as twelve different wavelengths.

In one embodiment, a method of monitoring tissue status or assessing a treatment modality is envisaged, including illuminating tissue with multiple wavelengths of filtered, polarized light, comparing the collected wavelengths to a mixture of known spectra, reconstructing local concentration variations of absorbing/light-scattering components comprising the tissue, calibrating the image by iteratively integrating parameters for each reconstruction point.

In a related aspect, calibrating includes arbitrarily assigning, at each pixel within an image, parameter values to each known component comprising the tissue, where parameter values are selected from a plurality of values, executing an algorithm to converge a calibration function comprising calculating calibration coefficients by fixing one or more parameters at one value and solving for other one or more parameters, thereby obtaining average calibration loop pixel parameter values, estimating the convergence between the fixed one or more parameter values and the other one or more parameter values, adjusting the calibration by imposing one or more spatial characteristics for the fixed one or more parameter values to smooth said values and repeating the above steps until one or more predetermined conditions are satisfied and converting reconstructed data to form output images, In a related aspect, areas of illumination correlate with tissue status or treatment efficacy.

In another related aspect, the converting is carried out according to the relationship:

$$I_{detected}(\lambda) = cI_{source}(\lambda)d(\lambda) \quad (7)$$

$$\frac{1 - e^{-\sqrt{A\mu_{a(dermis)}(\lambda)/\mu'_{a(dermis)}(\lambda)}}}{\sqrt{A\mu_{a(dermis)}(\lambda)/\mu'_{a(dermis)}(\lambda)}}$$

$$e^{-2t_{epi}\mu_{a(epi)}(\lambda)}$$

wherein $I_{detected}(\lambda)$ denotes the intensity of the tissue under examination at a defined wavelength;

c denotes an intensity scaling variable;

$I_{source}(\lambda)$ denotes the intensity of the collimated light source;

$d(\lambda)$ denotes the spectral response of the camera;

$\mu'_{s(dermis)}(\lambda)$ denotes transport corrected scattering coefficient of the dermis;

$\mu_{a(epi)}(\lambda)$ denotes the absorption coefficient of the epidermis;

$\mu_{a(dermis)}(\lambda)$ denotes the absorption coefficient of the dermis;

A denotes a real, positive constant that may be varied to allow for less than perfect Lambertian illumination; and $t_{epi}$ denotes thickness of the epidermis.

In a related aspect, the collected wavelengths are selectively processed to remove reflected light that corresponds to very short photon pathlengths, including selectively processing one or more gated optical imagers or one or more polarizers.

In another related aspect, comparing includes comparing the collected wavelengths to one or more mixtures of known spectra. Further, the illuminating light may be polarized.

In one aspect, parameter values are envisaged to include intensity of light reaching tissue surface, melanin volume fraction of epidermis, thickness of epidermis, blood volume fraction of dermis, oxygenated blood volume fraction of total blood volume, change in concentration of hemosiderin, change in concentration of oxy ferritin, change in concentration of redox ferritin, change in concentration of cytochrome b oxidase, change in concentration of cytochrome b redox, change in concentration of cytochrome c oxidase, change in concentration of cytochrome c redox, change in concentration of oxidase cytochrome c oxidase, change in concentration of oxidase cytochrome c redox, changes in other forms of cytochromes, changes in other analytes, or a combination of one or more thereof.

In a related aspect, multiple wavelengths comprise wavelengths in the visible and near-infrared (NIR) spectra, including, but not limited to, wavelengths between about 400 nm and about 2700 nm.

In another related aspect, the center wavelengths are envisaged to be about 500 nm, 520 nm, 540 nm, 560 nm, 580 nm, 730 nm, and 760 nm, and the full width half maximum (FWHM) is about 20 nm.

In another aspect, the center wavelength is envisaged to be about 800 nm, and the full width half maximum (FWHM) is about 30 nm.

In another aspect, the center wavelengths are envisaged to be about 840 nm and 880 mn, and the full width half maximum (FWHM) is about 40 nm.

For monochrome applications, it is possible to take advantage of both the bloom resistance of imaging sensors and experimental knowledge of the spectral filter response functions to dramatically extend the effective dynamic range of the sensor.

In another embodiment, a method of resolving high and low light intensities into informational contrast is envisaged, including, but not limited to, controlling illumination of an image scene by passing bands of wavelengths to an imager, identifying and quantifying the sensitivity of the pixels comprising the imager, acquiring one or more images; and correcting each pixel identified and quantified, where the steps result in extracting informational contrast from said light intensities.

In a related aspect, the imager is a CCD sensor or a CMOS sensor.

In another aspect, a further step comprises controlling illumination of an optically dense sample by passing specific wavelengths of light to each pixel comprising the imager.

In another related aspect, the method further includes characterizing the filter spectral response functions, accessing the raw pixel data and plotting neighboring pixels as a function of wavelength, where the plotting generates approximations of the spectral response function. In such a method, the gain setting may be fixed.

In another aspect, the sample is illuminated with light a source including a monochromatic light source, a narrow band light source a tunable laser, or a broadband light source.

In one aspect, a patterned filter is placed over a chip comprising the imager, where the patterned filter includes, but is not limited to, a Bayer filter.

Alternatively, the method may include determining the depth of penetration of photons before the photons reach a sensor comprising the imager. In a related aspect, determining includes, but is not limited to, application of a layered sensor.

In a related aspect, determining a Foveon spectral response function is envisaged including selecting one or more wavelengths; and selecting wavelengths that are used to image an object or acquiring a single image with a range of intensities, where an approximation of relative attenuation of the response function is obtained.

In another aspect, the steps extend the dynamic range of the imager.

In one embodiment, a device is envisaged including, but not limited to, a light source, an illuminator/collector, optional illumination wavelength selector, an optional light gating processor, an imager, a detected wavelength selector, a controller, an analyzer and a display unit, where the device resolves high and low light intensities into informational contrast by controlling illumination of an image scene by passing bands of wavelengths to an imager; identifying and quantifying the sensitivity of the pixels comprising the imager; acquiring one or more images; and correcting each pixel identified and quantified; wherein said steps result in extracting informational contrast from said light intensities.

To the accomplishment of the above and related objects, this invention may be embodied in the form discussed in the examples, attention being call to the fact, however, that these are illustrative examples only, and that changes may be made in the specific application of the invention.

DESCRIPTION OF THE PREFERRED EMBODIMENTS

Figure 1:
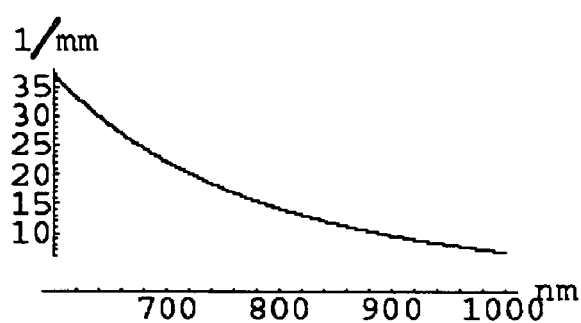
FIG. 1 shows melanin absorption coefficient as a function of wavelength.
Figure 2:
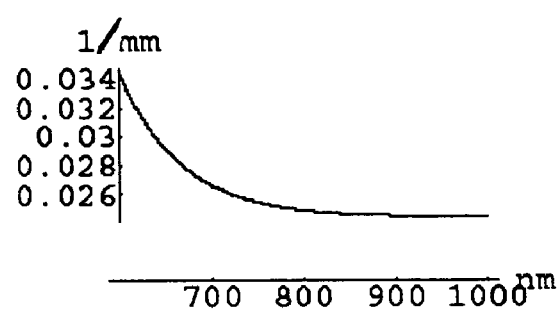
FIG. 2 shows skin absorption coefficient as a function of wavelength.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Definitions

The term "wavelength," including grammatical variations thereof, means the distance between points of corresponding phase of two consecutive cycles of a wave. In a related aspect, this term applies to a discrete group of wavelengths in a band identified by a center wavelength.

The term "dynamic range," including grammatical variations thereof, means in a system or device, the ratio of (a) a specified maximum level of a parameter, such as power, current, voltage, or frequency to (b) the minimum detectable value of that parameter.

The term "informational contrast," including grammatical variations thereof, means representative output that accurately communicates to a receiver the degree of difference between the lightest and darkest parts of a image.

The abbreviation "ISO" is a rating indicating the level of sensitivity to light for a device.

The term "calibration loop pixel parameter values," including grammatical variations thereof, means those pixels in the image selected, either automatically by an algorithm, or manually by the user, for the purposes of calibration feedback. These pixels which will generally at a minimum meet the requirement of informational contrast, as well as a determination that the pixels also have the capability to contain the relevant information on analyte concentrations being reconstructed by the algorithm which is being used.

The term "chromophore," including grammatical variations thereof, means functional groups with characteristic optical absorptions or molecules, cells, organelles, tissues or organs which contain them.

The term "optically dense medium," including grammatical variations thereof, means an object/matrix having high or relatively high opacity. For example, biological tissue such as skin (i.e., including dermal and epidermal layers) would be embraced by the term optically dense medium.

The term "tissue viability," including grammatical variations thereof, means the state of the tissue with regards to whether or not the tissue will survive if no further action is taken.

The term "tissue status," including grammatical variations thereof, means the current state of a tissue with respect to the current status of tissue reflectance/scattering components and viability.

The term "tissue oxygenation," including grammatical variations thereof, means oxygenated hemoglobin ratio of blood contained in the arteries, veins and capillary compartments of the sampled tissue volume.

The term "oxygenation," including grammatical variations thereof, means the ratio of hemoglobin carrying oxygen to the amount of hemoglobin that is oxygen depleted. In a related aspect, tissue oxygenation refers to the ratio of oxygenated to total hemoglobin in the blood contained in the arteries, veins and capillary compartments of the sampled tissue volume.

The term "blood volume or total hemoglobin," including grammatical variations thereof, means a combined measure of oxygenated and deoxygenated hemoglobin, which can be used as an indicator of tissue perfusion.

The term "hydration," including grammatical variations thereof, means the amount of fluid present both lack of or accumulation resulting in a significant decrease or increase in tissue volume.

The term "contact," including grammatical variations thereof, means a state of interaction or touching of the tissue with an apparatus. In a related aspect, non-contact refers to a state of immediate proximity without touching or disturbing the tissue.

The term "non-invasive," including grammatical variations thereof means a procedure whereby the tissue is unaltered from its present state and non-intrusive. In a related aspect, minimally invasive refers to a procedure whereby the tissue is minimally and unnoticeably adjusted to permit the apparatus to obtain meaningful measurements.

Figure 5:
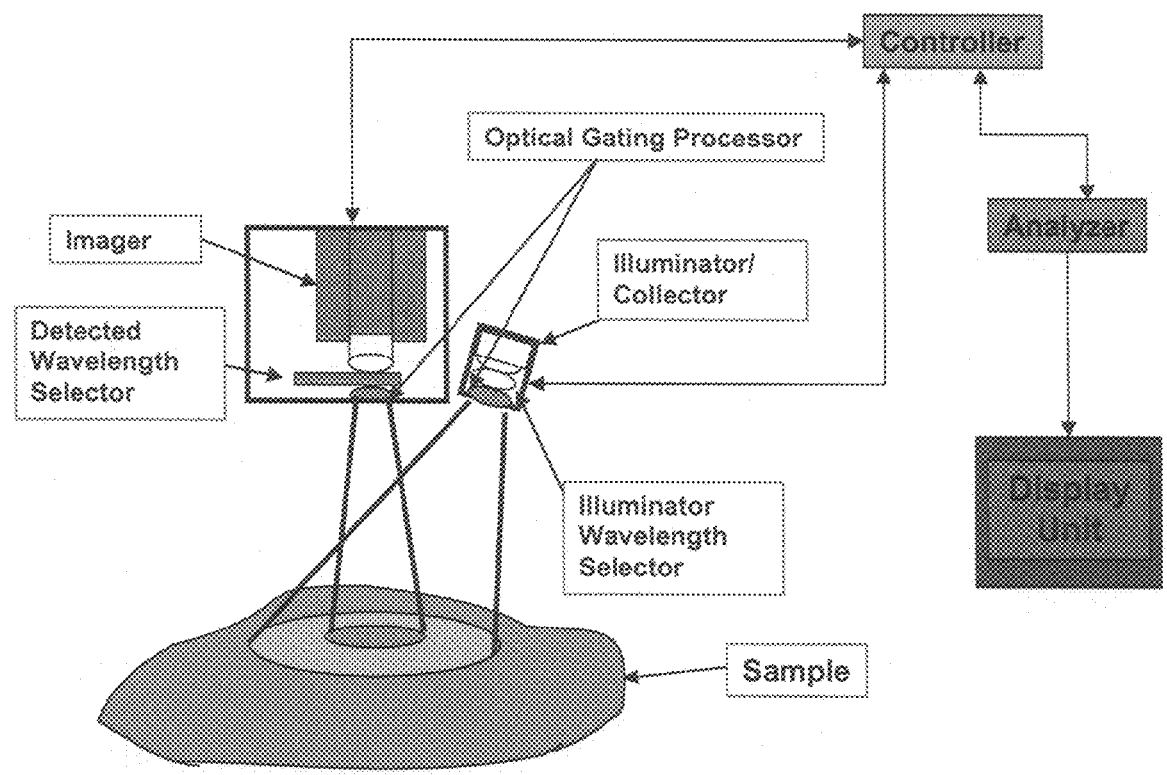
FIG. 5 shows a diagram of the device.

Described herein is a device for use in assessing tissue viability, status and health, as shown in FIG. 5. The device comprises a light source, an illuminator/collector, optional illumination wavelength selector, an optional light gating processor, a controller, an imager, a detected wavelength selector, an analyzer and a display unit. The apparatus provides information on tissue viability in a non-invasion manner utilizing visible and near infrared absorption image based spectroscopy.

The method transforms spectral image data into relative concentrations of analytes in tissue and/or structural parameters; these relative concentrations and parameters can provide both structural and functional contrast useful to the diagnosis and monitoring of disease or anomalies. A fundamental limitation is that the number of model parameters, which include the relative analyte concentrations, must be equal to or less than the number of discrete wavelengths captured by the spectral imager. The absorption spectra for each analyte of interest must be known at all wavelengths for which image data is collected.

The preferred embodiment of the invention is to select an anomalous condition and set of structural parameters (e.g., layer thickness(es)) and functional parameters (e.g., analyte concentrations) that provide desired information regarding the anomalous condition. Depending on the depth of the condition, different bands of illumination may be used. For very surfacy (0.1 to 0.5 mm) tissue results, some set of wavelengths of visible light may be best suited because the light penetrating deeper than the site of interest will generally be absorbed. For depths to 1 cm, near infrared light will provide better penetration. The preferred embodiment for deep anomalies is to use visible light with its limited penetration, but generally more feature-rich spectra, to characterize superficial structures and analytes (within approximately 0.5 mm of the surface). Then with knowledge of that superficial information, and the corresponding ability to predict how they will affect the transmission of light, use NIR light to obtain information on deeper structures and analytes.

Blood is a dominant chromophore in tissue. Therefore, when selecting chromophores of interest, blood must usually be included for accurate reconstruction. Variations in tissue blood volume fraction and blood oxygen saturation may also be of interest depending on the anomalous condition being imaged. During tumor growth, lipids are often excluded from the tissue volume so that a reduced lipid concentration may be partially indicative of tumor presence. Likewise, tissue volume fraction of water is often higher in tumors. Often it is sufficient to limit reconstruction to one or two parameters, or a combination metric, which reduces the number of wavelengths and therefore complexity of the imaging device. For example, the tissue volume fraction of deoxy hemoglobin may be used which is the product of the tissue volume fraction of blood times the blood volume fraction of deoxy hemoglobin. Another dominant chromophore which is highly variable between patients is melanin. Melanin is generally confined to the epidermis which may vary in thickness due to location on the body and inflammatory activity associated with a disease state. Depending on the number of wavelengths available from the imager, these four parameters (blood volume, blood saturation, melanin concentration, and epidermis thickness) may be made free for the model to optimize, or may be fixed at some sacrifice to reconstruction accuracy. Illuminance on the tissue must be a free parameter because it is both essential for reconstruction and highly variable due to the shape of the tissue surface and geometry with respect to the illumination source, as well as spatial non-uniformity of the illumination source. Thus, generally at least 5 wavelengths of spectral image data are needed for any study. We will call these the principle variables of our method. We will call additional analytes optional analytes.

Figure 3:
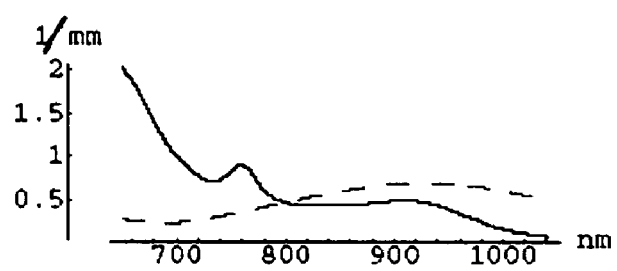
FIG. 3 shows absorption coefficient for oxy-hemoglobin and deoxy-hemoglobin shown as a function of wavelength.
Figure 4:
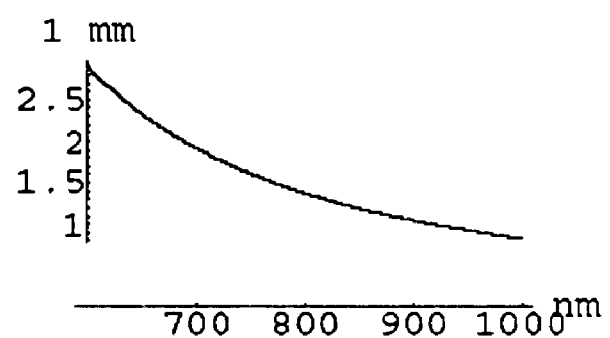
FIG. 4 shows transport-corrected scattering coefficient in skin as a function of wavelength.

Before using the spectrum for any of the principle or optional analytes, their spectra are convolved with the spectral response functions of the imager being used. For example, if each of the band-pass filters on a six-band imager has a full width at half max (FWHM) of 50 mm, much of the detail will be lost. For the blood data, the deoxy response between 750-800 nm, shown in FIG. 3, would be largely gone. Conversely, a properly designed spectral imaging system will have a spectral response that retains as much detail of distinguishing features as necessary. In the preferred embodiment, the center and bandwidth of the filters are designed to capitalize on distinguishing features in the spectra. Hence, one filter will typically have a center at the deoxy peak and a FWHM of approximately 20 nm.

Multispectral Imaging
Description of Generalized Layered Model

The intensity of the source of the sample is a function of wavelength $I_{source}(\lambda)$. In one embodiment, the invention describes a model that illustrates how this intensity is reduced as it travels through layers and is reflected back from layers in the sample. In a related aspect, layers may be defined by changes in scattering and/or absorption coefficient, or by statistical properties of photons traveling through turbid media (e.g., related to polarization blocking reflected light and absorption limiting the depth of penetration for specific wavelengths).

In another related aspect, the model used for the top layer depends on several factors. For greatest penetration of the light, collimated illumination from the source is generally preferred. For collimated illumination and a top layer thickness that is much less that the transport-corrected scattering length, $1/\mu'_s$, Beer's law may be used to compute the intensity after passing through the top layer $$I_{top} = I_{source}(\lambda) e^{-t_{top}\mu_{a(top)}(\lambda)} \tag{8}$$

wherein $\mu_{a(top)}(\lambda)$ is absorption coefficient for the layer and $t_{top}$ is the thickness. The absorption coefficient may be broken into parts such as volume fractions of analytes, or concentration of components. This is where the link between the model and the concentration or volume fractions of specific pigments, or absorbing dyes which are in the layers come into the model. The user must determine the expected dominant absorbers for each layer in the sample. It is more effective to be too inclusive than less, where the former results in driving the complexity and the number of wavelengths upward.

Equation 7 is particularly well suited to the case where cross-oriented polarizers are used because back reflected photons in the thin layer can be assumed to be blocked by the polarizers. Preferably, an arbitrary top layer should be used to account for the behavior of the photons if cross-polarization filters are used in the imaging system.

In the absence of the polarizers and when the first layer is thick, the top layer may use a diffuse transmission through a slab formula such as $$I_{trans\text{-}top} = I_{source}(\lambda) \tag{9}$$

$$\frac{e^{-2\mu_{a(top)}(\lambda)/\mu'_{a(top)}(\lambda)} \{\cosh[\sqrt{A\mu_{a(top)}(\lambda)/\mu'_{s(top)}(\lambda)}\,] - 1\}}{\sqrt{A\mu_{a(top)}(\lambda)/\mu'_{s(top)}(\lambda)}}$$

$$\sinh[t_{top}\sqrt{6\mu_{a(top)}(\lambda)/\mu'_{s(top)}(\lambda)}\,]$$

where $\mu'_{s(top)}(\lambda)$ is the transport-corrected scattering coefficient of the top layer and $t_{top}$ is the thickness, where the thickness is non-dimensional and geometry-corrected.

The second layer may be modeled as having a finite thickness if significant light detected by the imager has passed through the layer to deeper points in the sample. Since the light is no longer collimated at this layer interface, a slightly different form of Eq. 9 may be used $$I_{trans-layer} = I_{from-layer-above}(\lambda) \frac{\cosh\left[\sqrt{A\mu_{a(layer)}(\lambda)/\mu'_{s(layer)}(\lambda)}\right] - 1}{\sqrt{A\mu_{a(layer)}(\lambda)/\mu'_{s(layer)}(\lambda)} \sinh\left[t_{layer}\sqrt{6\mu_{a(layer)}(\lambda)/\mu'_{s(layer)}(\lambda)}\right]} \quad (10)$$

Using Eq. 9 and Eq. 10, the method may be employed to extract concentrations and volume fractions of tissue analytes from transillumination images of layered tissue. For the transillumination geometry, excluding short pathlength photons is not required.

The diffuse reflectance from thick layers must be propagated back through the overlaying layers to the detector. The diffuse reflectance from these layers is $$I_{ref-layer}(\lambda) = I_{from-layer-above}(\lambda) \quad (11)$$

$$2\frac{1 - \cosh\left[\sqrt{A\mu_{a(layer)}(\lambda)/\mu'_{s(layer)}(\lambda)}\right]}{1 - e^{t_{layer}\sqrt{A\mu_{a(layer)}(\lambda)/\mu'_{s(layer)}(\lambda)}}}$$

$$\sqrt{A\mu_{a(layer)}(\lambda)/\mu'_{s(layer)}(\lambda)}$$

With a sufficient number of wavelengths (i.e., assuming the data from different wavelengths have independent information), and arbitrary number of layers can be chosen so that the layer of interest is well sample; the absorption of superficial layers is low enough that sufficient light makes it to the layer, and the absorption is high enough that the light entering the underlying layers is mostly absorbed, or that the underlying layers can be completely ignored. In the latter case, the simplified form of Eq. 11 may be used $$I_{ref-bottom}(\lambda) = I_{from-layer-above} \frac{1 - e^{-\sqrt{A\mu_{a(bottom)}(\lambda)/\mu'_{a(bottom)}(\lambda)}}}{\sqrt{A\mu_{a(bottom)}(\lambda)/\mu'_{s(bottom)}(\lambda)}} \quad (12)$$

In a related aspect, Eq. 11 may be used as the bottom layer if virtually all of the light going to deeper layers is absorbed so that it doesn't return.

Once the properties of some layers have been calculated, it may be possible to use a deeper penetrating set of wavelengths and add additional layers to the model so that the properties deeper in the sample may be obtained.

The absorption coefficients and the transport-corrected scattering $\mu'_s$ may not be generally reconstructed because as each additional wavelength is added, the number of unknowns increases by two. It is not possible to ignore scattering since it controls the path length over which absorption occurs and thus the amount of absorption by pigments or absorbing dyes in the layers of the sample. Given that the information most desired is related to absorption, the best approach is to determine an a-priori form for the scattering. An alternative approach with two unknowns is to use a weighted mix of Rayleigh and Mie scattering. Thus, it is possible to reduce the number of unknowns related to scattering to only two terms $$\mu'_s(\lambda) \approx M\lambda^{-B} + R\lambda^{-4} \quad (13)$$

where M is the Mie component weight, β is the scatter power, and R is the Rayleigh component weight.

The detector of the system has some spectral response characteristics that shape the light diffusely reflected from the surface of the sample $$I_{detected}(\lambda) = cI_{reflected}(\lambda)d(\lambda) \quad (14)$$

where $d(\lambda)$ is the spectral response of the camera and c is a scalar intensity gain factor. This intensity gain factor may be different at each pixel in the image. The gain factor also accounts for local geometry of the surface with respect to both the light source and detector, as well as factors previously mentioned such as light lost in specular reflections and photons that experience polarization preserving scattering near the surface.

A preferred embodiment is to choose between 2-6 wavelengths that penetrate a maximum of two actual or effective layers. For a thin superficial layer with a thick second layer, the above may be expressed as $$I_{detected}(\lambda) = cI_{source}(\lambda)d(\lambda) \quad (15)$$

$$\frac{1 - e^{-\sqrt{A\mu_{a(bottom)}(\lambda)/\mu'_{a(bottom)}(\lambda)}}}{\sqrt{A\mu_{a(bottom)}(\lambda)/\mu'_{a(bottom)}(\lambda)}}$$

$$e^{-2t_{top}\mu_{a(top)}(\lambda)}$$

The product of $d(\lambda)$ and $I_{source}(\lambda)$ is generally combined into a single calibration function for the imaging device. In a related aspect, the exponential factor 2 accounts for the light passing through the layer going to the deeper layer and the diffuse reflectance from the deeper layer passing through again as it travels to the detector.

After solving Eq. 15, deeper penetrating wavelengths may be used and a new model may be generated that includes a diffuse reflectance layer between the thin top layer and a bottom layer. The properties from the bottom layer of Eq. 15 will be used in the middle layer of the new model.

Tissue Model

The epidermis is typically 0.1 mm thick which is approximately the mean scattering distance of photons in tissue. Scattering in tissue is typically very anisotropic with $g \approx 0.9$. This means that the few epidermal scatterings will typically be shallow angle and the transmission through the layer may be considered to be independent of scattering. The intensity after passage through the epidermis is:

$$I_{epi} = I_{source}(\lambda)e^{-t_{epi}\mu_{a(epi)}(\lambda)} \quad (16)$$

where $I_{source}(\lambda)$ is the intensity of our collimated light source and $t_{epi}$ is the epithelial thickness. In practice, the air-tissue interface will have a specular reflection. To address this, the source and detector can have cross-polarized filters to block specularly reflected photons. Cross-polarized filters will also block most back-reflected photons that are scattered in the epidermis. In practice, these two components are accounted for by a scalar intensity scaling factor in the model.

The underlying dermis is where blood vessels are located and may also contain the anomalous site. This layer may be assumed to be a finite-thickness layer (for cases where the anomalous site is below the dermis), or infinitely thick (for anomalous sites in the dermis). For practical purposes with dermal diseases, attenuation of the signal as depth increases means that is often sufficient to assume the dermis is infinitely thick. This assumption also reduces the dimensionality of the model which may be important given limited spectral data. The light passing from the epidermis is no longer collimated due to epidermal scattering.

The diffuse reflectance is obtained at a point on the epidermis/dermis layer boundary from a broad area of Lambertian illumination:

$$I_{ref\text{-}dermis}(\lambda) = I_{epi} \frac{1 - e^{-\sqrt{A\mu_{a(dermis)}(\lambda)/\mu'_{a(dermis)}(\lambda)}}}{\sqrt{A\mu_{a(dermis)}(\lambda)/\mu'_{a(dermis)}(\lambda)}} \quad (17)$$

where A is a real, positive constant that may be varied to allow for less than perfect Lambertian illumination.

We may then express the intensity detected by a camera as follows:

$$I_{detected}(\lambda) = cI_{source}(\lambda)d(\lambda) \quad (18)$$

$$\frac{1 - e^{-\sqrt{A\mu_{a(dermis)}(\lambda)/\mu'_{a(dermis)}(\lambda)}}}{\sqrt{A\mu_{a(dermis)}(\lambda)/\mu'_{a(dermis)}(\lambda)}}$$

$$e^{-2t_{epi}\mu_{a(epi)}(\lambda)}$$

where $d(\lambda)$ is the spectral response of the camera. The product of $d(\lambda)$ and $I_{source}(\lambda)$ is generally combined into a single calibration function for the imaging device. This leaves an intensity scaling variable c which we reconstruct.

Equation 18 contains the five principle variables (some within the respective layer $\mu_a$ term), $V_{oxy}$, $V_{blood}$, $V_{mel}$, c, and t, that we wish to reconstruct. Additional optional analytes may be added to the model via the respective layer absorption coefficient. The baseline skin spectra by default contains components from normal concentrations of all analytes. For anomalous conditions, the normal mix of analytes may be perturbed. If this is suspected, it may be desirable to add one or more optional analytes to the model. For each layer, one may include a delta concentration term, $\Delta C$, which modifies the respective layer equation and may have a positive or negative value. For the dermis, Eq. 3 may be modified as follows:

$$\mu_{a(derm)}(\lambda) = V_{blood}\mu_{a(blood)}(\lambda) + (1 - V_{blood})\mu_{a(skin)}(\lambda) +$$
$$\Delta C_{optional\text{-}analyte(1)}$$
$$\mu_{a(optional\text{-}analyte(1)} + \alpha C_{optional\text{-}analyte(2)}$$
$$\mu_{a(optional\text{-}analyte(2)} + \quad (19)$$

The invention has been tested with optional analytes in the dermis. These analytes include cytochromes b, c and oxidase c, all in both oxy and redox states, as well as oxy ferritin redox ferritin, and hemosiderin. Perturbations in hemosiderin and cytochrome concentrations are associated with tumor activity. The contrast from these analytes provides functional information on the spatial nature of tumor metabolism. Changes associated with drug and/or radiation therapy can provide useful clinical information on patient response. For anomalous sites below the dermis, Eq. 10 can be used for diffuse transmittance through a finite layer. The light transmitted to this third, sub-dermal layer, will be diffusely reflected from that semi-infinite layer which contains the relevant absorbers. That reflectance will need to be modified by transmission through a diffuse layer on the return path through the dermis. In that manner, a three layer model may be constructed.

In the preferred embodiment, Eq. 18 is solved using a traditional non-linear least squares algorithm using a commercial package such as Mathematica, or directly using a numerical method code such as Levenberg-Marquardt. In practice, the range of acceptable values for the principle variable and optional analyte concentrations must be constrained to reasonable values. In the preferred embodiment, this is accomplished using a penalty function that is added to the least-squares solution. The penalty function is zero for reasonable values of the variable, but rapidly becomes large if the algorithm picks values outside of the reasonable range.

Calibration

The calibration term $d(\lambda)I_{source}(\lambda)$ in Eq. 18 may be obtained by taking a spectral image sequence of a calibrated diffuse reflecting source. The average pixel values in some region of the image may be used as the basis of a correction factor for that wavelength. There will be a correction factor for each wavelength of the spectral image. The correction factors correct all wavelengths to the same value when used with the calibrated diffuse reflecting source. Those correction factors may then be used on each pixel at respective wavelengths in tissue images. This method has the benefit of being more accurate in absolute terms. This type of calibration must be repeated often since the spectral characteristics of the source lamp may change with environment and lamp age.

Alternatively, we have developed a forward model calibration method in which an image sequence of a good normal site on the patient may be used as a self-calibration reference. The result has the advantage that it will highlight differences between the two sites which may be more useful for many disease states, and may be used on data for which no other calibration data is available and the disease is located to known locations. In this method, a set of pixels meeting the predetermined criteria are selected to be the calibration pixels and for the first approximation of the calibration, all the pixels in the set are averaged. This is repeated for the same pixel set at each wavelength. Nominal values for each principle variable are put into the model. Note that the optional analyte concentrations should be zero. Further, while the specific value of a principle variable at any pixel might vary significantly from the nominal, on average over a larger region, the value should approach the average. That is why an averaging technique is used for this type of calibration. A correction factor for each wavelength is computed that makes the regional averages fit the forward model data. These correction factors are then used in Eq. 18 when running the algorithm on each pixel in the image data from the anomalous site.

In the most general case, it is not known which pixels in the image correspond to diseased or normal tissue. A pixel set may be selected that is a mixture of unknown diseased and normal tissue and our calibration method will provide contrast between the diseased and normal tissue. These is an expected loss of quantitative accuracy, however, the method will provide contrast between diseased and normal tissue, even where there is no prior distinction between tissue status in the calibration.

Calibration of a multispectral imaging system is a crucial but under-emphasized aspect of system performance. The calibration data is a set of weights that normalize system sensitivity to some arbitrary normal. The system sensitivity is a combination of the amount of energy in a particular filter band that is emitted by the light source with the integrated sensitivity of the detector to that energy. Each of those components is generally not known, but the net response can be (and is traditionally) estimated by imaging a calibrated or known reflectance standard.

In contrast, for the instant invention the calibration method is envisaged to use the diagnostic images themselves and is integrated with the overall analysis. A sophisticated layered model of light propagation in layered tissue and knowledge of reasonable ranges of parameter values, and the spatial characteristics of those parameters are used. When the model results don't yield reasonable parameter values or spatial characteristics, the system calibration is modified in a deliberate manner until the final results satisfy a-priori knowledge of light propagation in tissue under analysis. This iterative process starts with the parameters that dominant the solution and as the calibration function converges, less significant parameters are included so that the last details of convergence are controlled by the smallest contributors (i.e., fine-tuning).

The basic structure of the layered tissue model used in the calibration analysis as envisaged employs requires a nonlinear regression technique (e.g., Levenberg-Marquardt) to solve for various parameters comprising the model. Unknown parameters at each pixel point of the image include some of the following (i.e., listed in roughly the order of signal strength, with 1 being the strongest, and a listing of analytes that may be used in the model):

1. intensity of light reaching tissue surface
2. melanin volume fraction of epidermis
3. thickness of epidermis
4. blood volume fraction of dermis
5. oxygenated blood (oxy hemoglobin) volume fraction of total blood volume (parameter 4)
6. change in concentration or tissue volume of lipids from normal
7. change in concentration or tissue volume fraction of water from normal
8. change in concentration of hemosiderin from normal
9. change in concentration of oxy ferritin from normal
10. change in concentration of redox ferritin from normal
11. change in concentration of cytochrome b oxidase from normal
12. change in concentration of cytochrome b redox from normal
13. change in concentration of cytochrome c oxidase from normal
14. change in concentration of cytochrome c redox from normal
13. change in concentration of oxidase cytochrome c oxidase from normal
14. change in concentration of oxidase cytochrome c redox from normal and
15. changes in other forms of cytochromes or other analytes from normal Nonlinear regression often converges to invalid values (i.e., physically unreasonable values). The convergence is sensitive to noise in the inputs and also has problems when the magnitude of the effect of different parameters is very different (this is certainly the case for optically dense media such as skin). The epidermis filters light reaching the dermis, where 1-40% of the epidermis is melanin, which is a strong absorber of light. About 1-5% of the dermis volume is blood. The oxy blood volume fraction is 30% to 90% of blood (depending on the mix of vessels vs. arteries and for vessels how much metabolism is in the tissue compared to the blood source). The angiogenesis associated with some tumors often results in blood vessels that allow iron compounds to leak into the extravascular region of tissue. The presence of iron results in compounds like hemosiderin in the tissue. The cytochromes are a much smaller fraction. To resolve these analytes requires a high dynamic range imaging system (e.g., greater than 16 bit scientific cameras, or in the alternative, an extended dynamic range method for color CCD and CMOS imagers).

For such a model, the results may be sensitive to small changes in light source spectral characteristics before and after a calibration. In a related aspect, the calibration results are dependent on the way calibration is performed. In contrast, using traditional imaging system calibration methods such as a mirror to reflect light through the cross polarized filters caused artifacts that were due to the non-uniform spectral response of the polarization filters. Further, using a calibrated reflectance source caused similar problems, but confounded with a partial depolarization of the reflected light. Neither was a diffuse reflectance material not reliable as a calibration source. Also, if the relative exposure times between images with different filters is changed (i.e., to maximize the use of dynamic range), the calibration needs to be redone. But the spectrum of the calibration light source is different from the diffuse reflectance spectrum from tissue; one or more calibration images can saturate if the relative exposure times were optimized for tissue. Thus, a better way to calibrate and make the nonlinear regression converge to appropriate values was needed. Further, sometimes images are collected without performance of calibration during the same imaging sessions—resulting in problems getting the nonlinear regression to converge using previous session or following session calibration. Changes in light source spectral characteristics (intensity as a function of wavelength) during a given session can even reduce the effectiveness of traditional calibration methods performed during the session. It is believed that this is a contributing factor as to why other methods of performing multispectral imaging are unable to achieve the desired results.

The method as envisaged employs an iterative process that uses feedback to improve estimates of the system calibration. The feedback is based on an analysis of nonlinear regression results and is repeated many times. For each parameter, an ideal value is defined, as well as a min and max acceptable value. In one embodiment, which uses nonlinear regression, a forcing function is included that initiates when a parameter goes outside the reasonable range. The function attempts to keep parameters from going very far outside the reasonable range. In other embodiments, for some parameters, such as intensity, a smoothness requirement is also employed. Intensity is a function of distance from the illumination source, non-uniformities of the illumination pattern and incidence angle on the tissue which is a function of the gross tissue curvatures, as well as—at small scale—the texture of the skin. Since the light to be imaged has traveled through the tissue some distance, the small scale illumination differences resulting from texture of the skin should be removed to prevent artifacts in the reconstruction. Other parameters such as melanin and blood have reduced spatial smoothness constraints.

Ideally the images are collected such that the operator has employed the full dynamic range of the imager at each wavelengths/filter setting. This is generally problematic with traditional calibration techniques (requiring a new calibration for every change). In practice, saturating any pixel can have negative effects, and so should be avoided. If it does occur, all saturated pixels must be removed from the calibration loop.

In one aspect, substantially underexposed images may be preprocessed to use the full dynamic range of the imager. The resulting inter-pixel interpolation often improves results. Pixels below a threshold intensity should be removed from the calibration loop. At low intensities, contributions from the presence of specific analytes goes into the noise level of the imager. When this happens, the calibration loop feedback is noisy and can increase errors. In a related aspect, any pixels that include anything other than the desired tissue should be removed from the calibration loop. Obviously, clothing and background objects fall into this category. But even things like body hair or tattoos can cause problems proportional to the fraction of pixels they comprise of the total calibration loop pixels.

The model as envisaged allows for fixing one or more parameters at their ideal or at another value and solving for one or more other parameters. The following is an example of one way in which to implement the algorithm:

In the first iteration, calibration coefficients are calculated that make the average calibration loop pixel parameters exactly equal the ideal values.

In the next iteration, many values are fixed at their ideal and the model is allowed to only reconstruct parameters such as intensity and melanin. Spatial smoothness criteria can be imposed on the intensity parameter and then that value can be used in the next iteration.

The calibration is then adjusted by using the new knowledge of intensity, but with all other parameters remaining at their ideal values.

In the next iteration, intensity at each pixel is fixed to the respective smoothed value as determined in the previous iteration, some parameters are fixed to their ideal and some other parameters are solved for, such as melanin and blood volume. Those reconstructed parameters are filtered to meet the respective spatial smoothness qualities.

The calibrations are readjusted at the given intensity, in view of the new knowledge of melanin, and blood volume.

In the next iteration, intensity is fixed as before, and one of the reconstructed parameters such as melanin is fixed to its new value. Other parameters are fixed to their ideal and solved for blood volume and oxy blood fraction. Spatial smoothness functions are imposed on those parameters.

Finally, all of the above parameters may be fixed and solved for one or more of the remaining coefficients that may be informative, along with respective spatial smoothness criteria. For example, with 6 filters, only 6 out of the many parameters listed above can be technically solved for.

At each step, several error measures may be calculated (i.e., at each pixel and globally) that are typically preserved for post analysis checks. In a related aspect, an algorithm that checks the error at each pixel against the mean and variance on each iteration can be employed. Pixels that exceed some threshold can be removed from the calibration loop of the future iterations with the justification that the pixel is an outlier and doesn't conform to the model (e.g., hair, tattoo, etc.).

One embodiment includes one or more additional filters and will enable reconstruction for the blood parameters of the superficial tissue separately from the deeper tissue using a similar method as described above, but including additional iterations.

Extension of Dynamic Range

To enable the use of inexpensive commodity imaging sensors in many scientific or biomedical applications, dynamic range greater than native dynamic range of the sensors are required. This can be done by controlling the lighting of the scene via employing monochromatic or narrow band width light or by filtering the light arriving at the camera to limit it to a particular band. The same technique can be used to extend the dynamic range of more costly scientific imagers as well.

For example, a very intense scene with light at a wavelength in the band of high sensitivity for a given pixel (with virtually all light passing through the respective Bayer filter), can saturate a red pixel and also excite to a lesser degree the neighboring green and blue pixels. It is envisaged that, for example, by knowing the filter spectral response functions of the red, green and blue parts of a Beyer filter, an image can be generated with much larger dynamic range than possible from the analog to digital converters (ADC) at each pixel.

In a related aspect, for example, for a particular wavelength being imaged, if there is a saturated red pixel, but a neighboring green pixel that is not saturated and the green filter response is known at the particular wavelength has a 16× greater attenuation than red, the red pixel's response can be estimated as if that pixel had dynamic range 4 bits larger than it actually has. Thus, an 8 bit sensor will approximate a 12 bit sensor and an 12 bit senor will approximate a 16 bit sensor. Likewise, if the green is also saturated but blue is not saturated and the filter response is known to be attenuated 128× over red, the red pixel's response can be estimated with the effective dynamic range of 19 bits (assuming a 12 bit native device).

In one embodiment, most crucial steps of this method are: 1) to characterize the filter spectral response function, and 2) to find a way to access the native pixel data. Many commercial cameras offer a mode that preserves the raw, un-interpolated pixel data. This raw data may be used with fewer artifacts than that typically associated with processed output data, however, such data is usually in a proprietary format which is non-trivial to use. It is assumed that either access to the raw data is possible or artifacts from native interpolation algorithms are acceptable.

In one embodiment, the CMOS Bayer filter or effective Foveon spectral response functions is first determined experimentally. In a related aspect, a variable, narrow band light source (e.g., tunable laser or broadband light source and monochrometer) is used to evenly illuminate a flat white object—or ideally a calibrated reflectance standard—and images are taken with the light source set at each of a plurality of wavelengths. In another related aspect, the image exposure, aperture, and sensor gain (ISO setting) will be fixed while taking images, or corrected for before calculating the spectral response functions.

Plotting neighboring pixels (with different overlying Bayer filters) as a function of wavelength will generate first approximates of the spectral response functions. This method is the most flexible and allows for future images to be taken at any wavelength within the range tested. In another related aspect, the intensity of the source is changed and a plot of the respective color pixel responses are taken.

In another embodiment, the Bayer/Foveon filter response functions may be obtained by choosing one or more wavelengths of interest and repeating the following for each wavelength to obtain attenuation ratios at just those wavelengths. In a related aspect, the selected wavelengths should be the ones that will be used for actual imaging, meaning that this approach is less flexible than the above, but simpler to implement and can be more accurate. In another related aspect, the simplest approach is to take a single image with a range of intensities. For example, an image in which a laser beam is focused on a diffuse scattering media may be seen in FIG. 10. In such a scattering media, the laser intensity falls off exponentially with increasing distance from where the laser hits the media. Red, green and blue pixels at the same distance from the laser can be expected to have identical intensity. From this assumption, an approximation of the relative attenuation of the three Bayer filter/Foveon components may be obtained.

In another related aspect, to obtain a better estimate of the relative filter attenuations, a model of pixel behavior is used with the spectral response data obtained above before calculating the attenuation ratios. The pixel model should account for noise and various non-linear behaviors. All imaging devices are ultimately limited by shot noise which is proportional to $$1/\sqrt{N_p} \tag{20}$$

where $N_p$ is the number of photons hitting a pixel. For most detectors operating at room temperature, other sources of noise typically dominate. Generally, the most significant noise sources include dark current, photoresponse no-uniformity and pixel-reset noise. Photoresponse non-uniformity is due to non-uniform capacitances between pixels and is proportional to signal intensity. This noise will limit signal-to-noise ratio (SNR) most at high intensities. This source of noise can be reduced by mapping pixel responses, given a uniformly illuminated target. From a map, a correction can be applied to each pixel. Pixel-reset noise is proportional to temperature and related to the transistor structure of the CMOS pixels. In a related aspect, this noise can be somewhat reduced by lowering image sensor temperature. Dark-current is determined by defects in the image chip silicon substrate. This noise is proportional to temperature and will probably have the greatest effect on images, since it reduces SNR most at long image times with low intensity. When attempting to extend dynamic range of an image, the challenge is to resolve signals at both very high and low intensities, thus all sources of noise should be included in the pixel response model for the best results.

In a related aspect, the simplest pixel intensity correction has the following form:

$$I_{corrected} = (I_{cmos} - I_{darkoffset})G_{pnr} \tag{21}$$

where $I_{darkoffset}$ is subtracted from the pixel intensity measured by the sensor, $I_{cmos}$. The darkoffset is essentially the A/D count that would be obtained in a dark scene given the chip gain/ISO, exposure time and temperature, and arises from the dark-current. In a related aspect, it can be practically estimated from pixels near the edge of the chip that are covered by a dark mask. These pixels may be interrogated if access to the raw image data is available. In more stringent imaging cases, a dark image may be taken and actual values at each pixel in the image may be used in Eq. 21. The photoresponse non-uniformity is the $G_{pnr}$ variable gain factor which will be different for each pixel and must be obtained from an image of a uniform or calibrated white standard. In a related aspect, it may be satisfactory to set this value to 1 for all pixels.

Figure 6:
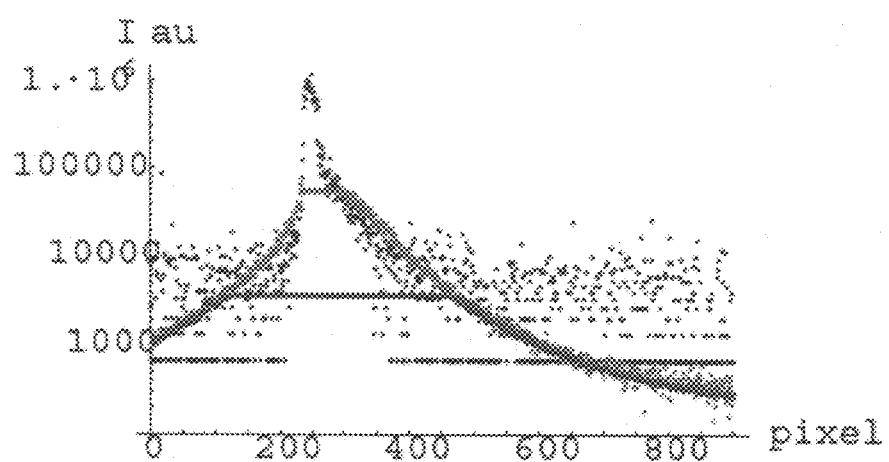
FIG. 6 shows a line-scan of raw CMOS pixel data.

Pixels near $I_{darkoffset}$ will have a much higher shot-noise level as may be seen in the blue pixels in FIG. 6. Thus, before calculating the attenuation ratios, it is usually best to only select those pixels above some threshold above $I_{darkoffset}$, and those below some threshold below $I_{saturation}$. In one embodiment, given a 12 bit image with $I_{darkoffset}=128$ and $I_{saturation}=4095$ the calculation of rations may be limited to those pixels with $300<I_{cmos}<4000$. Once these pixels are identified, Eq. 21 is used to calculate the corrected intensity for each pixel/color and ratios are calculated with any neighboring pixels of different colors (to ensure approximately the same pixel intensity) meeting the above criteria.

In another embodiment, a simple interpolation method is used, such as bilinear interpolation, to obtain the three colors at each pixel, especially if the test image is of relative uniform intensity, then identify if one or two pairs (or possibly three, but for red and blue wavelengths, where the greatest dynamic range extension is possible, three pairs, less so) of colors at that pixel which meets the criteria. For those color pairs that meet the criteria, the ratio is calculated. In a related aspect, some pixel locations will have no pixels that meet the criteria, however, such an observation is not absolutely adverse. Subsequently, the average pixel attenuation ratios can be calculated for the color pair. Further, attenuation ratios will be directly obtained for red/green and green/blue, but not for red/blue. In such a case, the red/green and green/blue ratios may be multiplied to obtain the red/blue ratio.

In another related aspect, once the attenuation ratios have been obtained, a different smart algorithm is necessary to create an extended dynamic range image. Generally, a simple interpolation algorithm will be used to obtain an estimate of all three colors at each pixel. At each pixel, the three colors are classified according to the $I_{darkoffset}$, $I_{saturation}$ and thresholds as described above into three categories: noise-band, mid-band, and saturation-band. If one or more colors are in the mid-band range, they are intensity corrected using Eq. 21 and then corrected for color using the respective color ratio attenuation values and subsequently averaged (if more than one color) for the final extended dynamic intensity value. Sometimes, no color at a pixel will be in the mid-band. In that case, a decision is made if the color with the smallest attenuation factor is used (since it is most likely to be signal rather than noise). If all are in the saturation band, the color with the greatest attenuation is used (since this most likely to be a valid rather than fully saturated pixel).

In a related aspect, the significant measure for obtaining informative attenuation ratios is to correct pixel intensities so that the resulting intensities are linear. In one embodiment, this is accomplished by using Eq. 21. In related aspect, non-linear factors at the top and bottom end of the sensor response can cause significant errors. The thresholds for choosing pixels may be made more stringent, but at some point the number of acceptable pixels meeting the criteria will become too small and sampling errors will cause problems in calculating the attenuation ratios. Further, these same non-linearities will cause distortion in reconstruction of an image. In another embodiment, a more sophisticated model accounts for a gamma factor in pixel intensity response, as well as a more important noise bias error at low intensities that must be subtracted from the pixel intensity. This yields an alternative to Eq. 21 as follows:

$$I_{corrected} = [\{I_{cmos} - I_{darkoffset} - Ae^{-B(I_{cmos} - I_{darkoffset})}\}G_{pnr}]^\gamma \tag{22}$$

where γ will typically be near 1 and A and B are related to the noise statistics of the sensor operating at a given gain/ISO, exposure time, and temperature.

The following examples are intended to illustrate but not limit the invention.

EXAMPLES

Example 1

Multispectral Analysis

Figure 7:
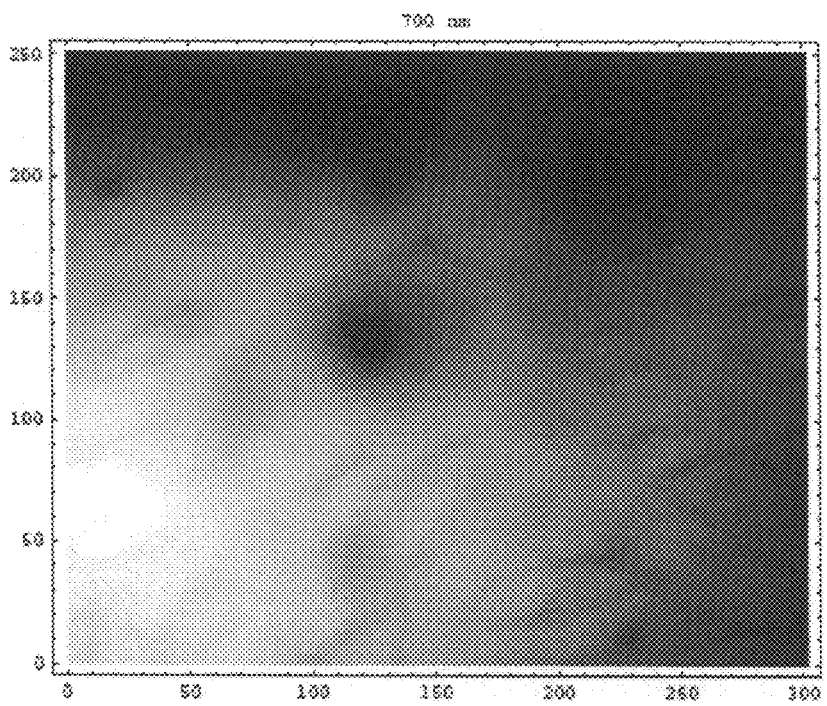
FIG. 7 shows image taken at 700 nm of a vascular skin tumor.

The disclosed invention may be used to obtain medically relevant functional and structural contrast from multispectral images. There are some commercially available multispectral imaging system and a number of ways of building multi-spectral imaging systems that are known to those skilled in the art. Typically such systems have a broad-band illumination source, a wavelength selecting device such as a filter wheel or tunable LCD filter on either the camera or illumination source, and an imager such as a CCD camera. The method was tested on data obtained using a CCD-based spectral imager that captures 512×512 pixel images at six wavelengths using a filter wheel on the camera (NIR at 700, 750, 800, 850, 850, 900 nm, with 50 nm FWHM and 1000 nm with 10 nm FWHM). While this is not generally the optimal choice of wavelengths and FWHM for the filters, it was sufficiently close to the optimal choice to show contrast as desired. The images have 16 bits per pixel such as shown in FIG. 7. The light source was a halogen lamp with a 600 nm long-pass filter. The NIR wavelength light penetrates into tissue farther than other wavelengths due to tissue's low absorption in the NIR. To further increase the penetration of detected light, polarization filters were used to selectively filter light that has only scattered a few times. One polarizing filter was placed on the illumination source after the long-pass filter. A cross-polarization oriented filter was placed before the filter wheel on the CCD camera. Thus, light scattered from shallow tissue and generally corresponding to very short photon path lengths in the tissue were blocked whereas the more scattered light depolarized and was detected.

The six spectral bands used for testing of the multispectral imaging method allow for the reconstruction of up to six unknowns. In this example, the method was applied to multispectral images of a vascular skin tumor. In this example, abnormal concentration of melanin in the epidermis and changes in blood volume and oxygen saturation were revealed by the invention at tumor sites (which may be seen as dark areas in FIG. 7). The biggest source of error in Eq. 18 is related to the change in $\mu'_s$ as function of wavelength. The change in path length is accounted for in Eq. 18, but as $\mu'_s$ decreases, the volume sampled by the photons increases. Since the tissue has both physical and biophysical structures, changing the sampling volume with wavelength changes the actual concentrations of sampled analytes as a function of wavelength.

Figure 8:
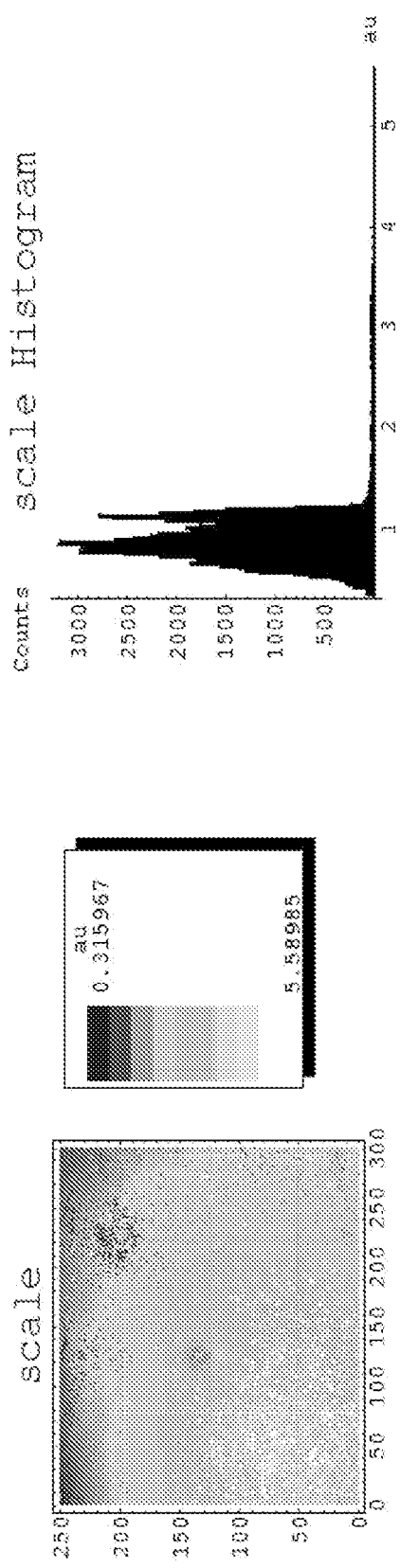
FIG. 8 shows contrast from reconstructed intensity scaling.
Figure 9:
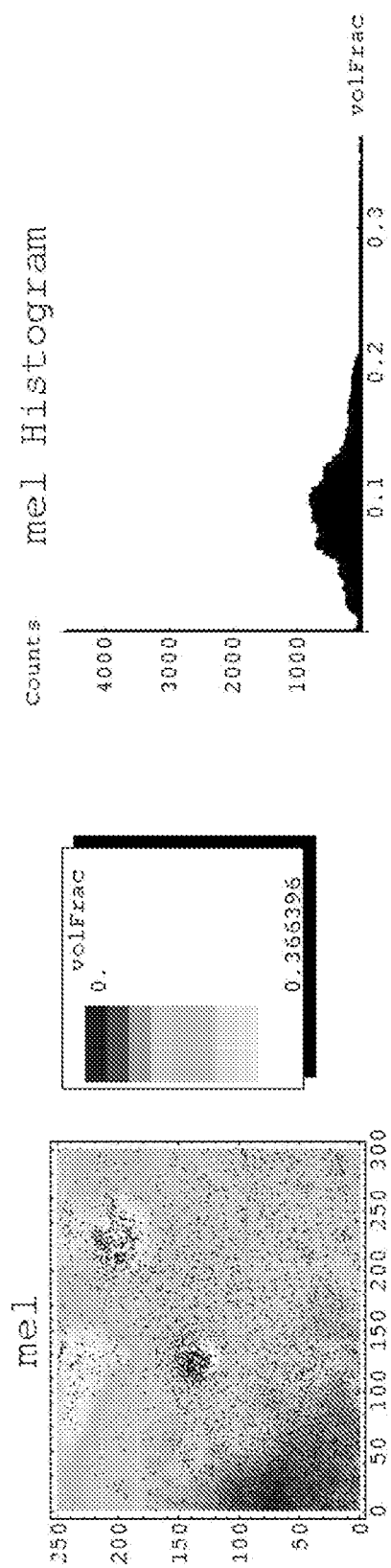
FIG. 9 shows contrast from reconstructed epidermal melanin volume fraction.
Figure 10:
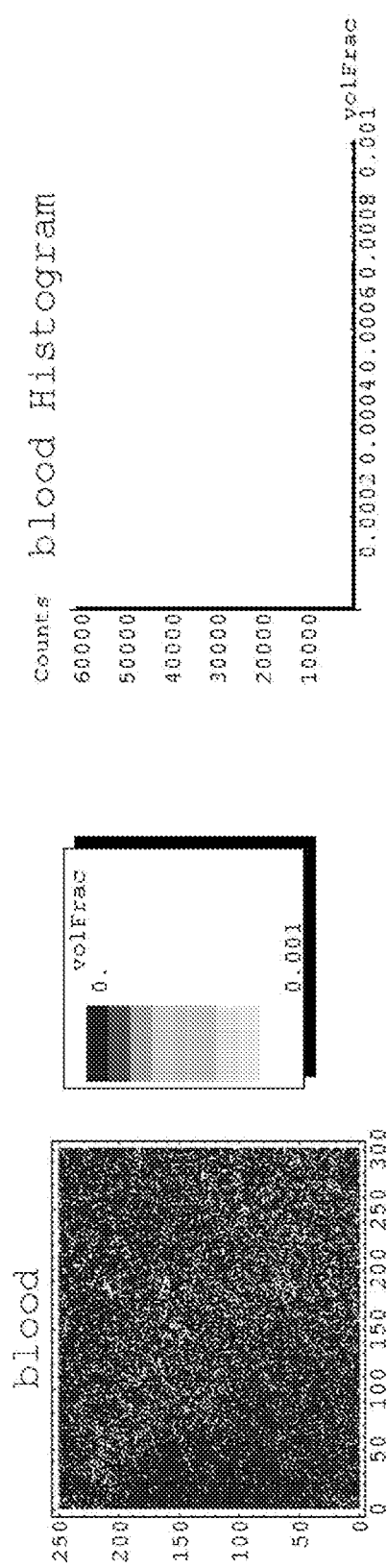
FIG. 10 shows contrast from reconstructed dermis blood volume fraction.
Figure 11:
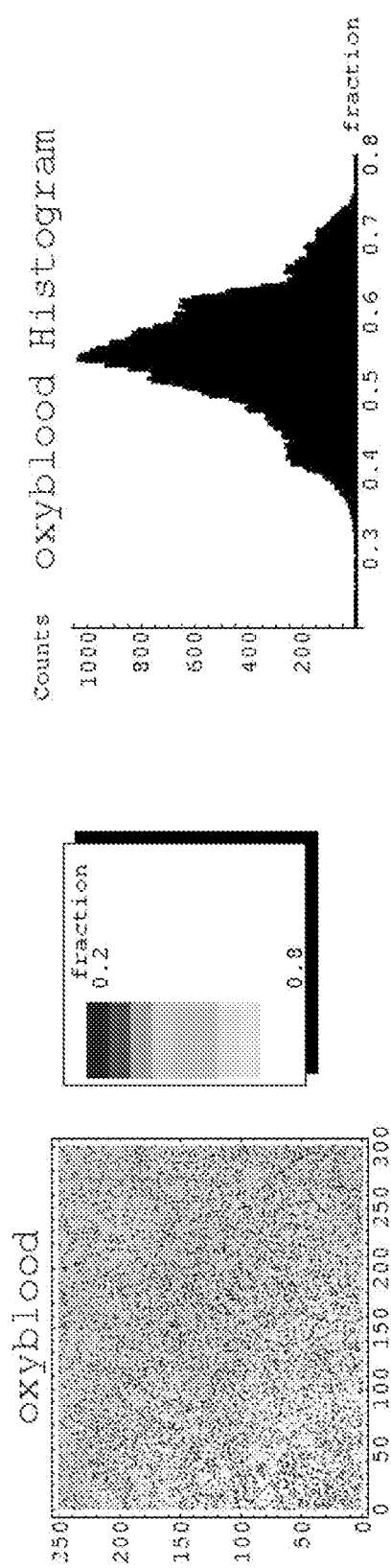
FIG. 11 shows contrast from reconstructed blood oxygen fraction.

The intensity scaling variable is shown as an image in FIG. 8. This image generally is not used diagnostically, but with an oblique light source can highlight raised areas on the tissue surface. Melanin distribution can often highlight areas in the skin with an abnormal condition such as shown in FIG. 9. The melanin histogram shows a distribution that is clustered around 0.1 which is well within expected values as published by Jacques. In the presence of tumors in the example, both hemosiderin and melanin are indicators of an abnormal condition and present confounding signals given their similar spectra and the choice of filters and wavelengths. In this example, the highest levels of melanin/hemosiderin occurs at tumor sites. Blood volume levels vary over a wide range. Where blood vessels are near the tissue surface, values are large as shown in FIG. 10. In other areas, blood volume is very low as expected. The fraction of oxygenated blood is potentially very useful in locating local ischemia which may be associated with a tumor. In this example, the tumor sites have lowered blood oxygen levels as is shown in FIG. 11.

The method has also been tested on data obtained using several different imaging systems; e.g., a CCD based spectral imager that captures 496×656 pixel images at five wavelengths using a filter wheel on the camera (NIR at 730, 760, 800, 840 and 880 nm, with a corresponding FWHM of 20,20, 30, 40 and 40 nm respectively). The images have 12 bits per pixel. The light source was a halogen lamp with a linear polarizer. A cross-polarization oriented filter was place before the filter wheel in front of the CCD imaging system.

Figure 12:
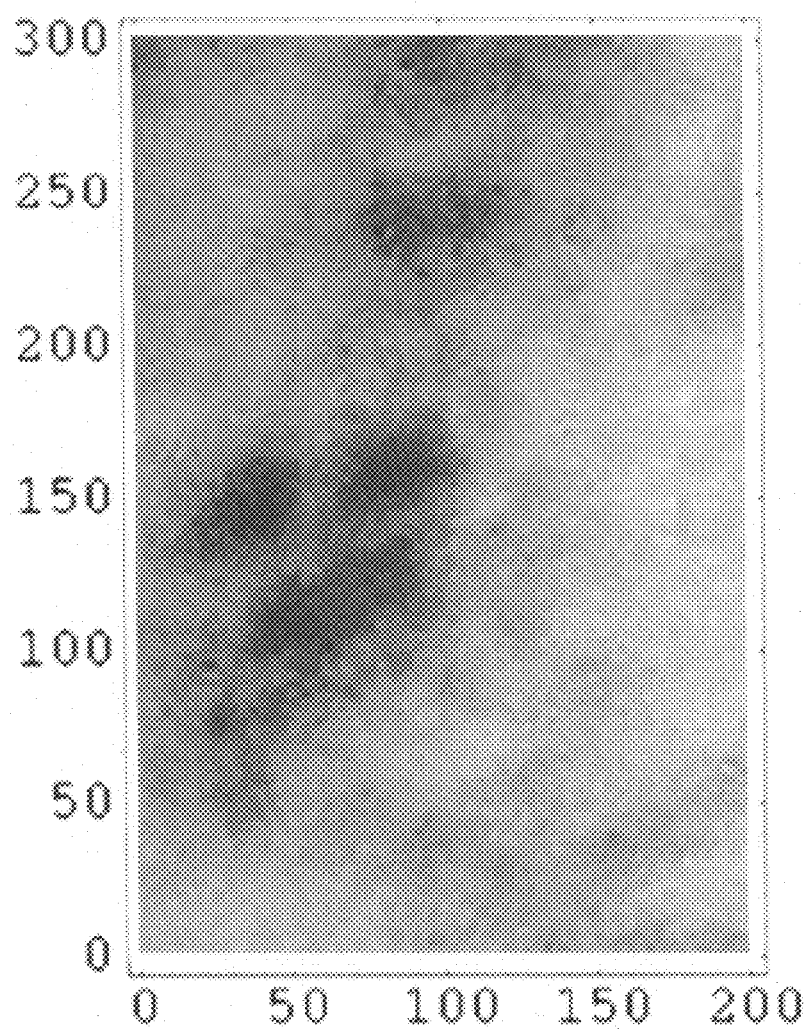
FIG. 12 shows visible light images taken of two lesions on a human foot.
Figure 13:
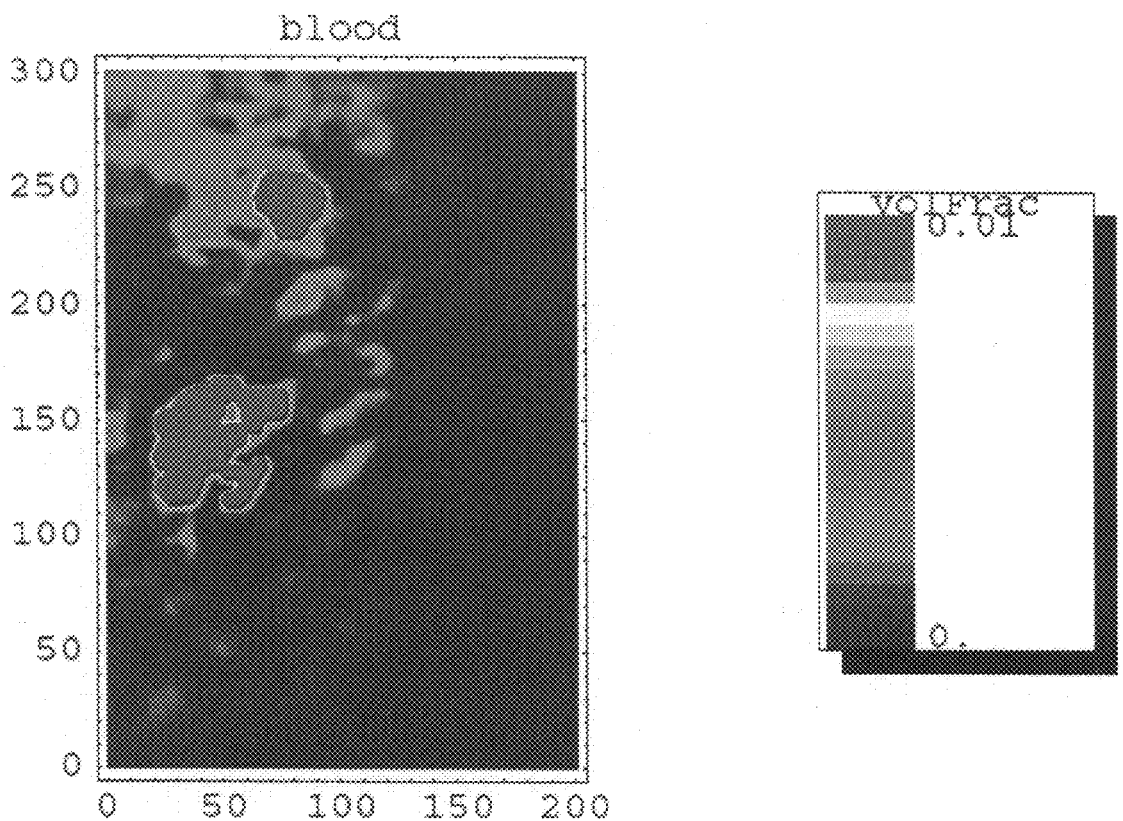
FIG. 13 shows the contrast from reconstructed dermis blood volume fraction of the tissue.

The five spectral bands used for testing of the multispectral imaging method allow for the reconstruction of up to five unknowns. The method was applied to multispectral images of a skin lesion. Changes in blood volume and oxygen saturation were revealed at lesion sites (i.e., the dark areas of the color image shown in FIG. 12). The top lesion is an abrasion in which the skin was not broken. The site has increased blood flow throughout, as may be seen in FIG. 13. In other areas, blood volume is very low as expected. The fraction of oxygenated blood is potentially very useful in locating skin ischemia which may be associated with a tumor and can be used to monitor wound healing and as a metric for vascular disease.

Figure 14:
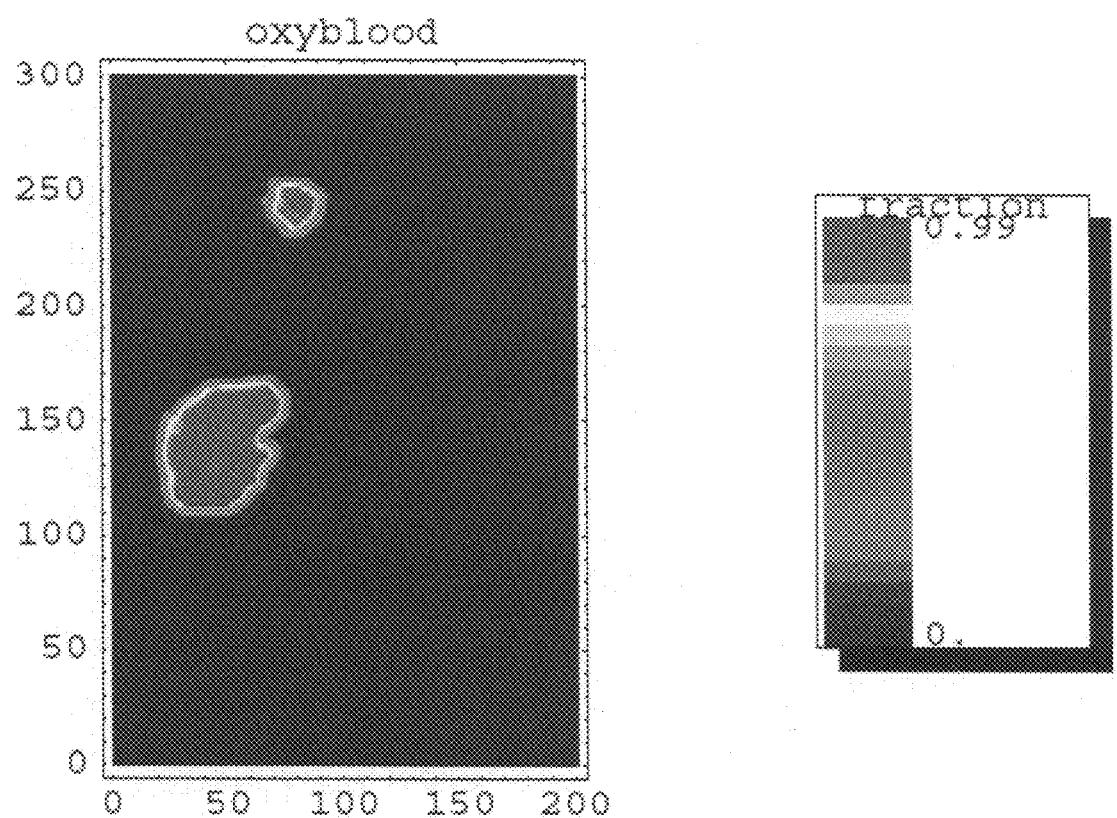
FIG. 14 shows the contrast from reconstructed blood oxygen fraction of the tissue.
Figure 15:
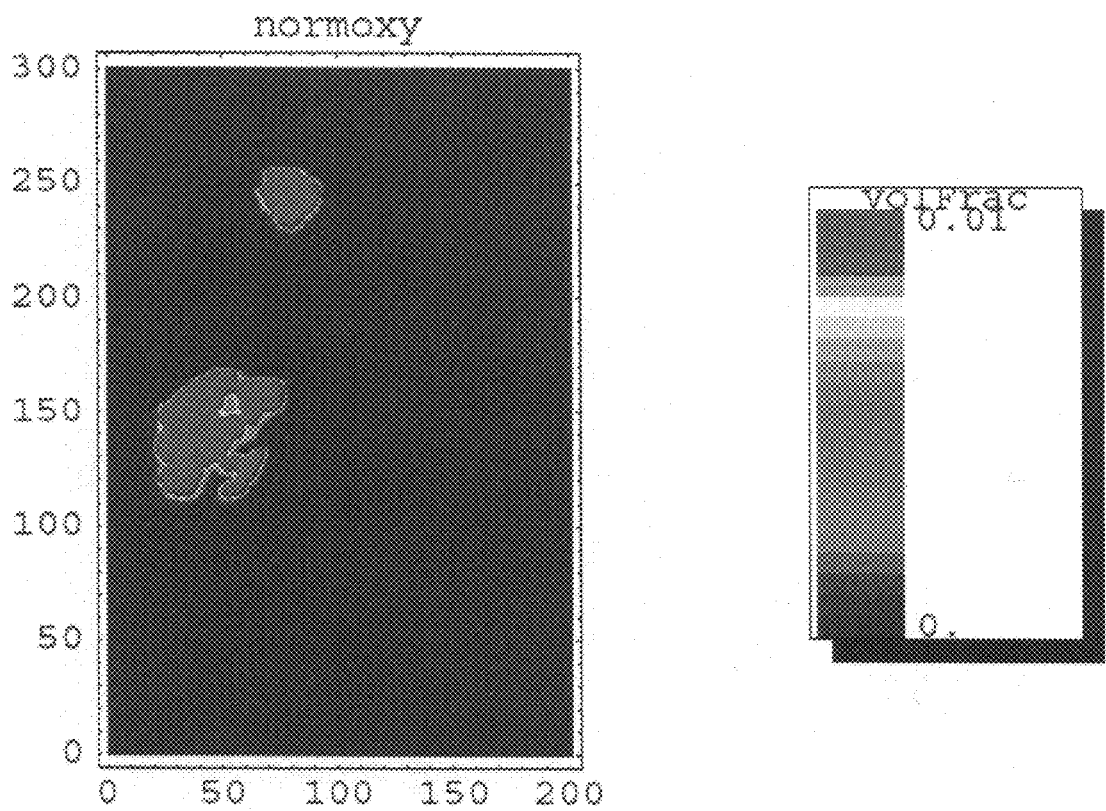
FIG. 15 shows the contrast from reconstructed normalized oxy-hemoglobin fraction of the tissue.
Figure 16:
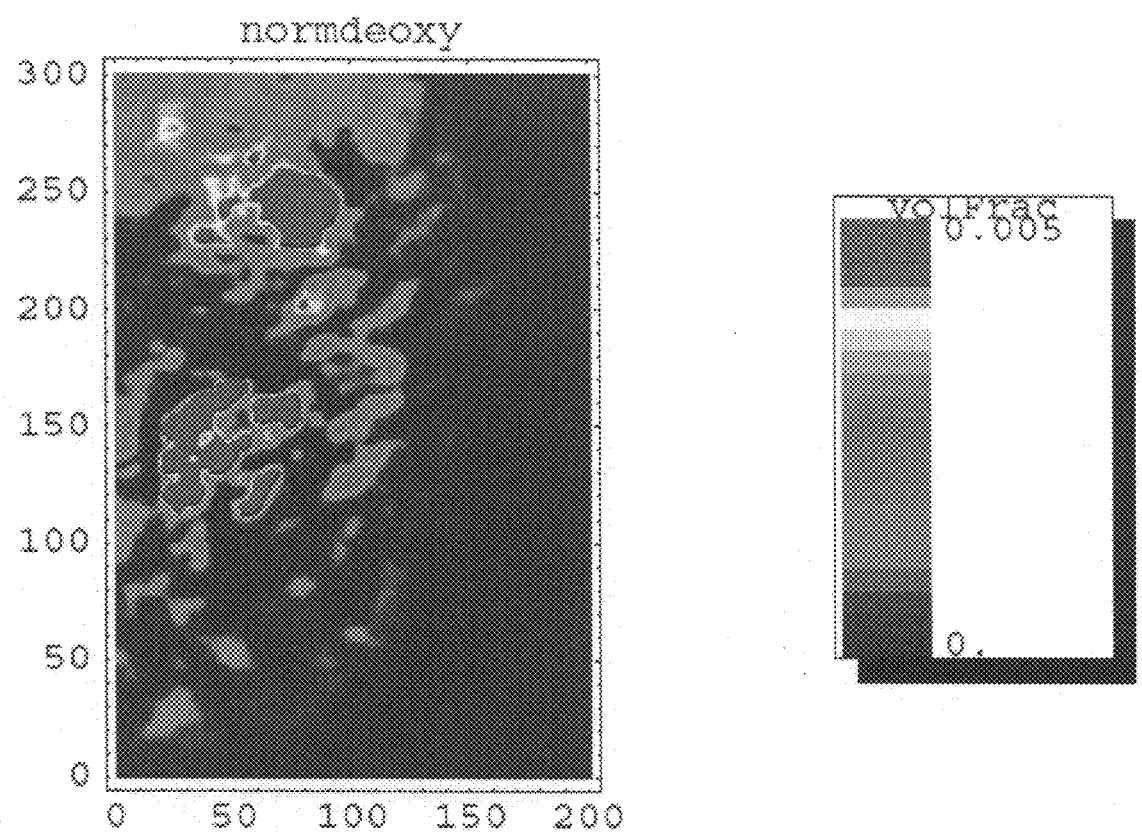
FIG. 16 shows the contrast from reconstructed deoxy-hemoglobin fraction of the tissue.

The lesion sites have higher blood oxygen levels as shown in FIG. 14. It is often more relevant to look at the relative amounts of total oxy-and deoxy-hemoglobin in the tissue. The tissue oxy-and deoxy-hemoglobin levels are shown in FIGS. 15 and 16. These last two images are computed from the tissue blood volume fraction and blood oxy-hemoglobin fraction model parameters. Areas of relatively high metabolism in the lesions may be seen in the tissue oxy-and deoxy-hemoglobin fraction images. The lower lesion had broken skin and is showing classical signs of high hemoglobin associated with healing at the periphery of the lesion as evidenced by the high hemoglobin relative to the interior of the lesion. By comparing the quantity of blood with relative levels of oxy-and deoxy-hemoglobin, the healing progress of the wound may be visualized.

Figure 17:
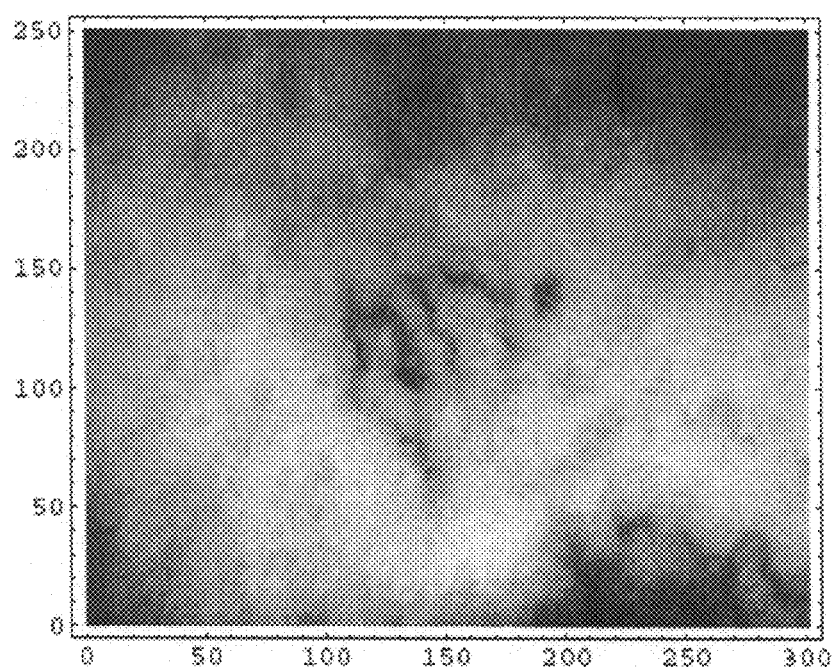
FIG. 17 shows a visible light image taken of spider veins.
Figure 18:
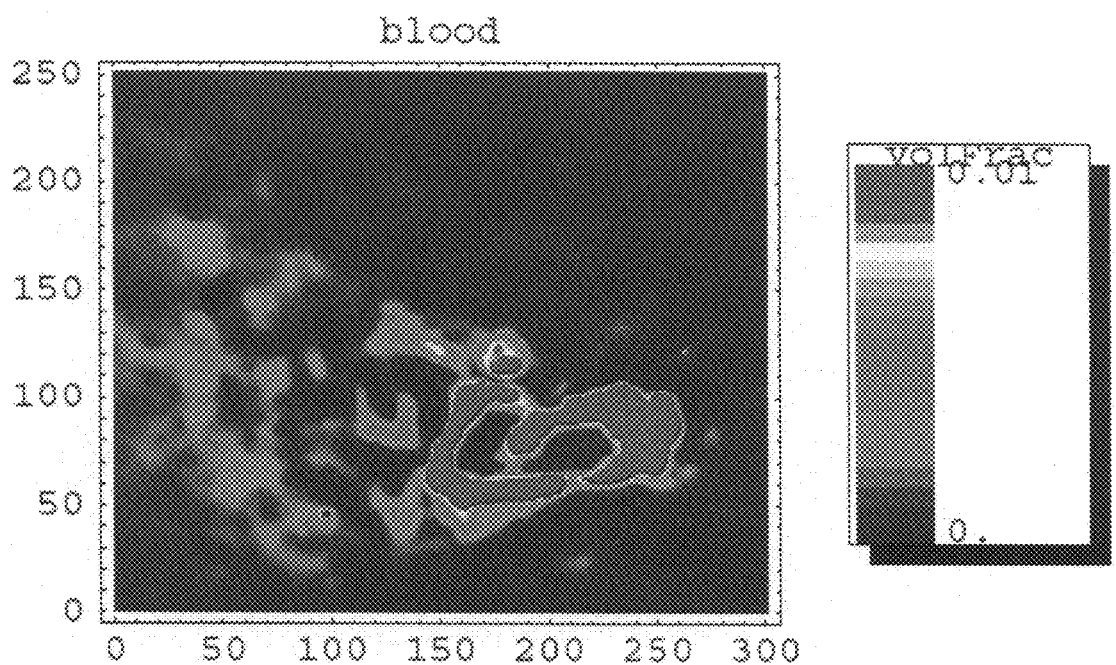
FIG. 18 shows the contrast from reconstructed dermis blood volume fraction of the tissue.
Figure 19:
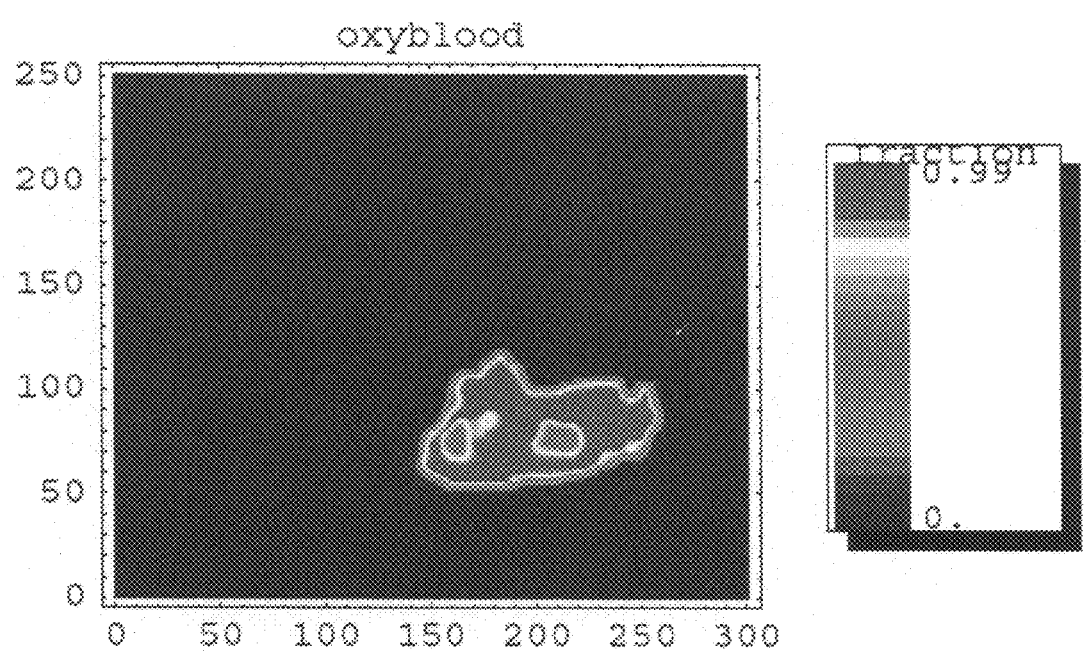
FIG. 19 shows the contrast from reconstructed blood oxygen fraction of the tissue.
Figure 20:
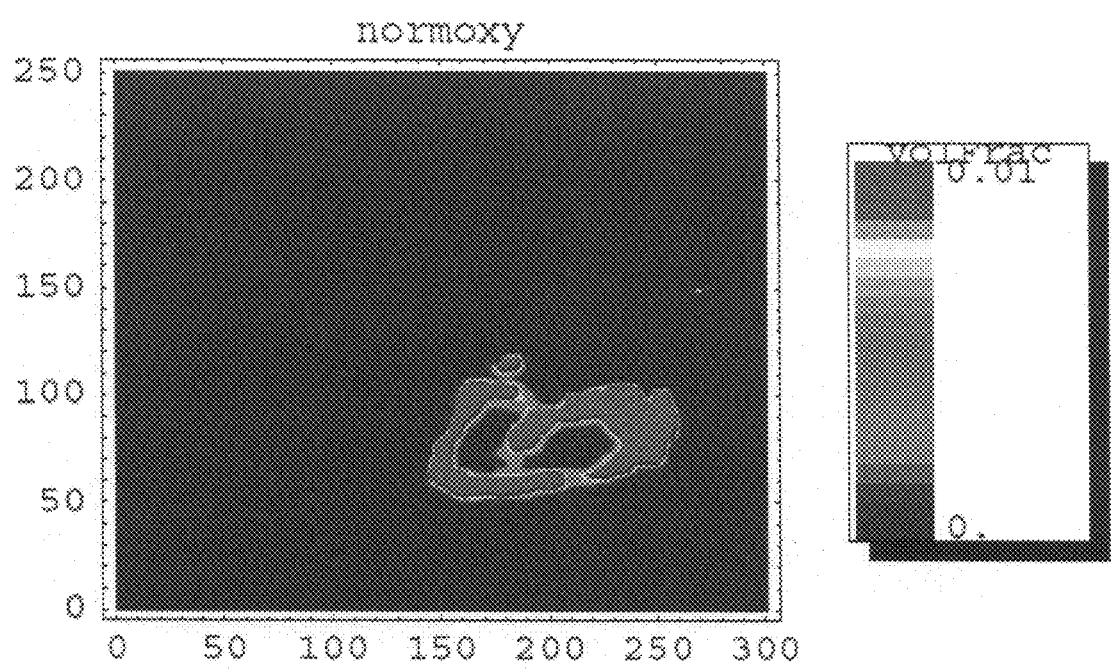
FIG. 20 shows the contrast from reconstructed normalized oxy-hemoglobin fraction of the tissue.
Figure 21:
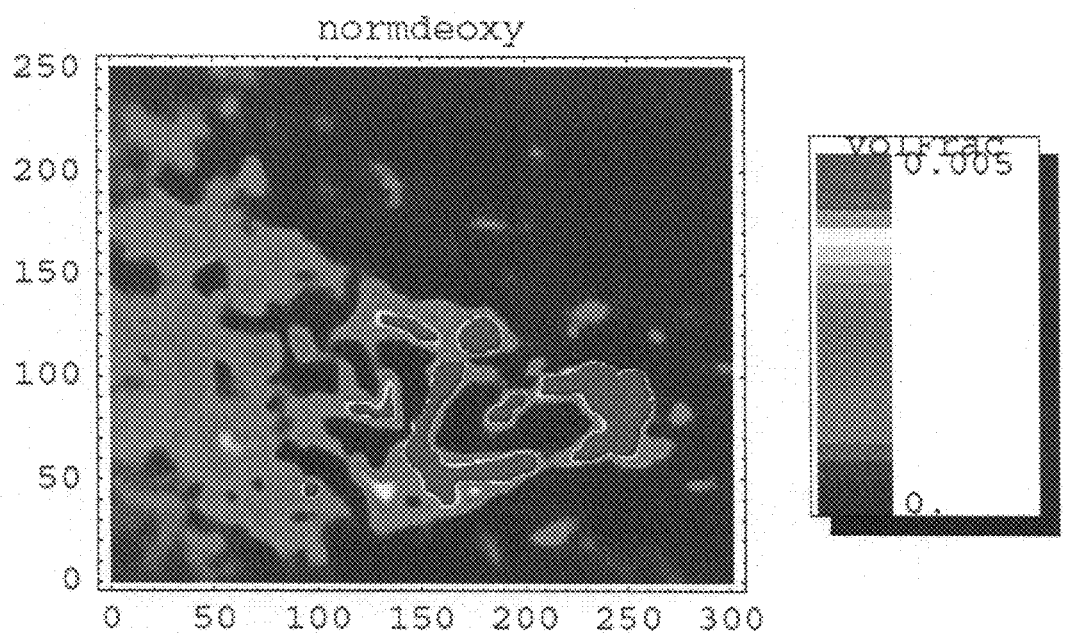
FIG. 21 shows the contrast from reconstructed normalized deoxy-hemoglobin fraction of the tissue.

In FIG. 17, a visible light image of spider veins is shown. At several points in the tissue blood volume is significantly elevated above the surrounding tissue as shown in FIG. 18. These elevated levels indicate regions where differences in the vasculature exist deep within the tissue and do not generally correspond to locations of the small vessels visible just below the surface. The same region has higher blood oxygen levels as may be seen in FIG. 19. Tissue levels of oxy-and deoxy-hemoglobin are also elevated above the surrounding tissue in the area of the spider veins as shown in FIGS. 20 and 21.

Example 2

CMOS Extended Dynamic Range

In biological tissue simulating phantom work that has already been completed, a commercially available CMOS-based color camera (Canon D-30) has been used to analyze the intensity-linearity of the pixels and the spectral response functions of the color filters on the pixels. [Additionally, a method was devised to access the raw 12 bit values, thereby bypassing the spatial filtering employed by the camera manufacturer to obtain satisfying color rendering] The method requires access to the raw pixel values (e.g., 12 bit on the Canon D-30) on the camera because it is necessary to bypass the spatial filtering which is often employed by consumer camera manufacturers to obtain satisfying color rendering. The method from obtaining raw values from an imaging device such as a CMOS device are described by the CMOS chip manufacturer's product data sheet or application instructions. Alternatively, some imaging systems include a method or instructions for obtaining raw pixel data such as the ".raw" format offered by Canon. For the Canon D-30, the pixel values in the ".raw" files are encoded using a lossless algorithm to reduce the file size.

For each 2×2 block of pixels in color CMOS imagers there are generally three different types of color filters overlaying those pixels in some specific pattern. In the case of the Canon D-30, there are two green filters (on one diagonal), one red and one blue filtered pixel (on the other diagonal). In addition to obtaining spectral response information from the CMOS manufacturer, there are two experimental ways to characterize the spectral response of the color filters: deterministic and statistical. In the deterministic method, a wavelength-selecting device such as a monochromator is used with a broad band illumination source to uniformly illuminate a uniformly reflective surface with selected narrow spectral band light. At each spectral setting, the luminance is measured with a power meter and a properly exposed image is acquired with known exposure settings (gain, aperture and integration time). After correcting to illuminance and each image's exposure setting, the normalized image intensity for each color pixel (or average of many or all of each color pixel) may be used as the transmission function for the respective color filter.

Often it is possible to use a simpler statistical measure that works best with an image set of a scene with a broad range of intensities and low spatial contrast (i.e., one or more images at each of the wavelengths used in a multispectral imaging system). Imaging sensors such as CMOS devices generally have a range of intensities in which the response is fixed and this known relationship is generally linear. Thus, as used herein, the term "linear" describes the range of known responses. At intensities lower than this linear range, noise dominates and the output becomes independent of the actual intensity. At intensities greater than the linear range, the sensor saturates at some maximum value (e.g., as 4095 for 12 bit imagers). The first step is to define a range of pixel counts that can be assumed to be within the linear range (e.g., 50-4050). Any pixel not in that range is excluded from further analysis. Next, for each wavelength used in the multispectral imaging system, the relative intensity of neighboring pixels of different colors, pair are averaged. Thus, the relative attenuation of the different color filters may be obtained for each wavelength in the imaging system.

Once the spectral response functions have been obtained for the color filters on the CMOS imager, an image with normalized intensity from all pixels in the linear range may be calculated. With the deterministic method, the wavelength transmission function first must be convolved with the bandpass of the imaging system. In the statistical method, if the same imaging system is used for filter characterization, the data is ready to use. Standard interpolation may be used to post-process the image which has the advantage that each non-linear pixel in the image will be replaced by an intensity-corrected value from neighboring pixels that are exhibiting a linear response.

In phantom experiments, a 633 nm diode laser was employed (with phantom scattering and absorption characteristics similar to those of tissue). The beam of laser light was multiply scattered and some of the light came out of the phantom and was imaged by the camera. The diffuse reflectance of light in highly scattering media experiences an exponential delay with offset from where the laser beam enters the phantom. Thus, to detect light at large distances from the insertion point, a large dynamic range sensor was required. The red laser light was very efficiently detected by the red pixels on the CMOS detector. FIG. 6 shows a line-scan of raw CMOS pixel data, before denoising but after scaling by filter response function coefficients, from an image of a 633 nm laser beam hitting a scaled phantom. Pixels in highest intensity region are saturated in all colors except blue. In low intensity areas, noise characteristics of red pixels are better than green and much better than blue. At positions near the beam, the red pixels were saturated at 4095 as seen in FIG. 6. At the beam center, all but the blue pixels were saturated. Where intensity was lower, greater than approximately 0.5 mm from the beam, the blue pixels captured only noise. For purposes of illustration, the data in FIG. 6 is shown for all pixels whereas in our method, pixels without informational contrast would be removed (e.g., the large noise shown by the blue pixels where the intensity is low would not corrupt the image data). For this case using only pixels with informational contrast, the corrected intensity data when including the green pixels with the red added approximately 4 bits of dynamic range. Adding the blue provided approximately 4 additional bits.

If there is sufficient knowledge of the image, the same image that is being dynamic-range extended may be used to determine the attenuation ratios. For images such as shown in FIG. 6, the ratios were calculated between neighboring pixels with different colors that were also approximately the same offset from where the laser hit the media (and that meet the mid-band intensity, or informational contrast criteria). The filter responses were such that approximately 20 bits of dynamic range could be captured in a single image on a 12 bit color sensor.

Although the invention has been described with reference to the above examples, it will be understood that modifications and variations are encompassed within the spirit and scope of the invention. Accordingly, the invention is limited only by the following claims.

REFERENCE LIST

1. A. H. Gandjbakhche and G. H. Weiss. Random walk and diffusion-like models of photon migration in turbid media. In E. Wolf, editor, *Progress in Optics*, volume 34, chapter 4, pages 333-402. Elsevier, Amsterdam, 1995.

2. S. L. Jacques and D. J. McAuliffe. The melanosome: threshold temperature for explosive vaporization and internal absorption coefficient during pulsed laser irradiation. *Photochemistry and Photobiology*, 53:769-775, 1991.

3. I. S. Saidi, S. L. Jacques, and F. K. Tittle. Mie and Rayleigh Modeling of Visible-light Scattering in Neonatal Skin. *Applied Optics*, 34(31): 7410-7418, 1995.

4. S. Wray, M. Cope, D. T. Delpy, J. S. Wyatt, and E. O. R. Reynolds. Characterization of the near infrared absorption spectra of cytochrome aa3 and haemoglobin for the non-invasive monitoring of cerebral oxygenation. *Biochimica et Biophsica Acta*, 933:184-192, 1988.

We claim:

1. A method of imaging a highly light scattering medium comprising:
   a) illuminating the medium with multiple wavelengths of filtered, processed light;
   b) calibrating an image by iteratively integrating parameters for each reconstruction point, wherein calibrating comprises;
      i) arbitrarily assigning, at each pixel within an image, parameter values to each known component comprising the medium, wherein parameter values are selected from a plurality of values;
      ii) executing an algorithm to converge a calibration function comprising calculating calibration coefficients by fixing one or more parameters at one value and solving for other one or more parameters, thereby obtaining average calibration loop pixel parameter values;
      iii) estimating convergence between the fixed one or more parameter values and the other one or more parameter values;
      iv) adjusting calibration by imposing one or more spatial characteristics for the other one or more parameter values to smooth said other one or more parameter values to form fixed one or more parameter values; and
      v) repeating steps (ii), (iii), and (iv) until one or more predetermined conditions are satisfied;

c) reconstructing local concentration variations of absorbing/light-scattering components comprising the medium, comprising comparing collected wavelengths; and
d) converting reconstructed data to form output images.

2. The method of claim 1, wherein reconstructing step (c) is carried out according to the relationship:

$$I_{detected}(\lambda) = cI_{source}(\lambda)d(\lambda)\frac{1 - e^{-\sqrt{A\mu_{a(bottom)}(\lambda)/\mu'_{s(bottom)}(\lambda)}}}{\sqrt{A\mu_{a(bottom)}(\lambda)/\mu'_{s(bottom)}(\lambda)}}e^{-2t_{top}\mu_{a(top)}(\lambda)}$$

wherein
$I_{detected}(\lambda)$ denotes the intensity of the medium under examination at a defined wavelength;
c denotes an intensity scaling variable;
$I_{source}(\lambda)$ denotes the intensity of the collimated light source;
$d(\lambda)$ denotes the spectral response of the camera;
$\mu'_{s(bottom)}\lambda$ denotes transport corrected scattering coefficient of the bottom layer;
A denotes a light and tissue interaction geometry factor;
$\mu_{a(top)}(\lambda)$ denotes the absorption coefficient for the top layer;
$\mu_{a(bottom)}(\lambda)$ denotes the absorption coefficient for the bottom layer; and
$t_{top}$ denotes thickness of a thin overlaying region.

3. The method of claim 1, wherein said collected wavelengths are selectively processed to remove reflected light that corresponds to very short photon pathlengths.

4. The method of claim 3, wherein the collected wavelengths are selectively processed by one or more gated optical image devices or one or more polarizers.

5. The method of claim 1, wherein reconstructing step (c) comprises comparing the collected wavelengths to one or more mixtures of known spectra.

6. The method of claim 1, wherein the light of step (a) is polarized.

7. The method of claim 1, wherein the light of step (a) is modulated to reduce extraneous background light.

8. The method of claim 1, wherein the parameter values are selected from intensity of light reaching the medium surface, chromophore volume fraction comprising one or more layers of the medium, thickness of one or more layers of the medium, or changes in concentration of the one or more chromophores, or a combination of one or more thereof.

9. The method of claim 1, wherein the multiple wavelengths comprise wavelengths in the visible and near-infrared (NIR) spectra.

10. The method of claim 9, wherein the multiple wavelengths are between about 400 nm and about 2700 nm.

11. The method of claim 1, wherein the medium is illuminated with at least two different wavelengths.

12. The method of claim 11, wherein the medium is illuminated with twelve wavelengths.

13. A method of monitoring tissue status or assessing a treatment modality comprising:
a) illuminating tissue with multiple wavelengths of filtered, polarized light;
b) calibrating an image by iteratively integrating parameters for each reconstruction point; wherein calibrating comprises:
i) arbitrarily assigning, at each pixel within an image, parameter values to each known component comprising the tissue, wherein parameter values are selected from a plurality of values;
ii) executing an algorithm to converge a calibration function comprising calculating calibration coefficients by fixing one or more parameters at one value and solving for other one or more parameters, thereby obtaining average calibration loop pixel parameter values;
iii) estimating convergence between the fixed one or more parameter values and the other one or more parameter values;
iv) adjusting calibration by imposing one or more spatial characteristics for the other one or more parameter values to smooth said other one or more parameter values to form fixed one or more parameter values; and
v) repeating steps (ii), (iii), and (iv) until one or more predetermined conditions are satisfied;
c) reconstructing local concentration variations of absorbing/light-scattering components comprising the tissue, comprising comparing collected wavelengths to a mixture of known spectra; and
d) converting reconstructed data to form output images,
wherein areas of illumination correlate with tissue status or treatment efficacy.

14. The method of claim 13, wherein reconstructing step (c) is carried out according to the relationship:

$$I_{detected}(\lambda) = cI_{source}(\lambda)d(\lambda)\frac{1 - e^{-\sqrt{A\mu_{a(dermis)}(\lambda)/\mu'_{s(dermis)}(\lambda)}}}{\sqrt{A\mu_{a(dermis)}(\lambda)/\mu'_{s(dermis)}(\lambda)}}e^{-2t_{epi}\mu_{a(epi)}(\lambda)}$$

wherein
$I_{detected}(\lambda)$ denotes the intensity of the tissue under examination at a defined wavelength;
c denotes an intensity scaling variable;
$I_{source}(\lambda)$ denotes the intensity of the collimated light source;
$d(\lambda)$ denotes the spectral response of the camera;
$\mu'_{s(dermis)}(\lambda)$ denotes transport corrected scattering coefficient of the dermis;
$\mu_{a(dermis)}(\lambda)$ denotes the absorption coefficient of the dermis;
$\mu_{a(epi)}(\lambda)$ denotes the absorption coefficient of the epidermis;
A denotes a real, positive constant that may be varied to allow for less than perfect Lambertian illumination; and
$t_{epi}$ denotes thickness of the epidermis.

15. The method of claim 13, wherein said collected wavelengths are selectively processed to remove reflected light that corresponds to very short photon pathlengths.

16. The method of claim 15, wherein the collected light is selectively processed by one or more gated optical image devices or one or more polarizers.

17. The method of claim 13, wherein reconstructing step (c) comprises comparing the collected wavelengths to one or more mixtures of known spectra.

18. The method of claim 13, wherein the light of step (a) is polarized.

19. The method of claim 13, wherein the parameter values are selected from intensity of light reaching tissue surface, melanin volume fraction of epidermis, thickness of epidermis, blood volume fraction of dermis, oxygenated blood volume fraction of total blood volume, change in concentration of hemosiderin, change in concentration of oxy ferritin, change in concentration of redox ferritin, change in concentration of cytochrome b oxidase, change in concentration of cytochrome b redox, change in concentration of cytochrome c oxidase, change in concentration of cytochrome c redox, change in concentration of oxidase cytochrome c oxidase, change in concentration of oxidase cytochrome c redox, changes in other forms of cytochromes, changes in other analytes, or a combination of one or more thereof.

20. The method of claim 13, wherein the multiple wavelengths comprise wavelengths in the visible and near-infrared (NIR) spectra.

21. The method of claim 20, wherein the multiple wavelengths are between about 400 nm and about 2700 nm.

22. The method of claim 13, wherein the tissue is illuminated with at least two different wavelengths.

23. The method of claim 22, wherein the tissue is illuminated with twelve wavelengths.

24. The method of claim 22, wherein center wavelengths are about 500 nm, 520 nm, 540 nm, 560 nm, 580 nm, 730 nm, and 760 nm, and wherein full width half maximum (FWHM) is 20 nm.

25. The method of claim 22, wherein a center wavelength is about 800 nm, and wherein full width half maximum (FWHM) is 30 nm.

26. The method of claim 22, wherein center wavelengths are about 840 nm and 880 nm, and wherein full width half maximum (FWHM) is 40 nm.

\* \* \* \* \*